US012792146B2

(12) United States Patent
Li et al.

(10) Patent No.: US 12,792,146 B2
(45) Date of Patent: Nov. 10, 2026

(54) MOTION DATA PROCESSING METHOD AND MOTION MONITORING SYSTEM

(71) Applicant: SHENZHEN SHOKZ CO., LTD., Shenzhen (CN)

(72) Inventors: Meiqi Li, Shenzhen (CN); Lei Su, Shenzhen (CN); Xin Zhou, Shenzhen (CN); Fengyun Liao, Shenzhen (CN); Xin Qi, Shenzhen (CN)

(73) Assignee: SHENZHEN SHOKZ CO., LTD., Shenzhen (CN)

(*) Notice: Subject to any disclaimer, the term of this patent is extended or adjusted under 35 U.S.C. 154(b) by 720 days.

(21) Appl. No.: 17/815,567

(22) Filed: Jul. 27, 2022

(65) Prior Publication Data

US 2022/0365600 A1 Nov. 17, 2022

Related U.S. Application Data

(63) Continuation of application No. PCT/CN2022/074377, filed on Jan. 27, 2022.

(30) Foreign Application Priority Data

Mar. 19, 2021 (WO) ................ PCT/CN2021/081931

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/1116* (2013.01); *A61B 5/296* (2021.01); *A61B 5/397* (2021.01);
(Continued)

(58) Field of Classification Search
CPC ....... A61B 5/1116; A61B 5/296; A61B 5/397; A61B 5/7225; A61B 5/14551;
(Continued)

(56) References Cited

U.S. PATENT DOCUMENTS

| | | | |
|---|---|---|---|
| 2004/0117212 | A1 | 6/2004 | Kong et al. |
| 2009/0012381 | A1 | 1/2009 | Kuramori et al. |

(Continued)

FOREIGN PATENT DOCUMENTS

| | | | |
|---|---|---|---|
| CA | 2914494 | A1 | 12/2014 |
| CN | 104706359 | A | 6/2015 |

(Continued)

OTHER PUBLICATIONS

First Examination Report in Indian Application No. 202217044592 mailed on Mar. 5, 2024, 5 pages.

(Continued)

*Primary Examiner* — Jennifer Robertson
*Assistant Examiner* — Nidhi N Patel
(74) *Attorney, Agent, or Firm* — METIS IP LLC

(57) ABSTRACT

A motion data processing method and a motion monitoring system provided in the present disclosure may process an electromyography (EMG) signal in the frequency domain or time domain to identify an abnormal signal in the EMG signal, such as an abrupt signal, a missing signal, a saturation signal, an oscillation signal, etc. caused by a high-pass filtering algorithm. The motion data processing method and the motion monitoring system may further perform a data sampling operation on the EMG signal through a data sampling algorithm, and predict data corresponding to the time point when the abnormal signal appears based on the sampling data, so as to obtain prediction data, and replace the abnormal signal by using the prediction data to correct the abnormal signal. The motion data processing method and
(Continued)

the motion monitoring system may not merely accurately identify the abnormal signal, but further correct the abnormal signal, so that the corrected data may be more in line with an actual motion of a user, thereby improving user experience.

20 Claims, 18 Drawing Sheets

(51) Int. Cl.

| | |
|---|---|
| ***A61B 5/11*** | (2006.01) |
| ***A61B 5/296*** | (2021.01) |
| ***A61B 5/397*** | (2021.01) |
| ***G06F 18/2415*** | (2023.01) |
| ***G16H 40/67*** | (2018.01) |
| ***G16H 50/20*** | (2018.01) |

(52) U.S. Cl.
CPC ........ *A61B 5/7225* (2013.01); *G06F 18/2415* (2023.01); *G16H 40/67* (2018.01); *G16H 50/20* (2018.01)

(58) Field of Classification Search
CPC ... A61B 5/0816; A61B 5/1121; A61B 5/1123; A61B 5/113; A61B 5/7253; A61B 5/7278; A61B 5/6803; A61B 5/7257; A61B 5/726; A61B 5/7405; A61B 5/7455; A61B 5/0022; A61B 5/6804; A61B 5/7207; A61B 5/725; A61B 5/72775; A61B 5/318; A61B 5/02055; A61B 5/02438; A61B 5/08; A61B 5/14542; A61B 5/24; A61B 5/389; A61B 5/1118; A61B 5/6802; A61B 5/746; A61B 5/11; A61B 5/6801; A61B 5/0205; A61B 5/1455; A61B 2562/0219; A61B 2505/09; A61B 2560/0223; G06F 3/015; G06F 3/011; G06F 3/017; G06F 18/2415; G06F 1/163; G06F 17/18; G06F 1/1684; G06F 2218/08; G16H 40/67; G16H 50/20
USPC ........................................................ 600/546
See application file for complete search history.

(56) References Cited

U.S. PATENT DOCUMENTS

| | | | | |
|---|---|---|---|---|
| 2009/0319459 | A1 | 12/2009 | Breazeal et al. | |
| 2011/0118621 | A1 | 5/2011 | Chu | |
| 2013/0116580 | A1 | 5/2013 | Liu et al. | |
| 2013/0173764 | A1 | 7/2013 | Kami | |
| 2014/0135960 | A1 | 5/2014 | Choi | |
| 2014/0207017 | A1 | 7/2014 | Gilmore et al. | |
| 2015/0045699 | A1 | 2/2015 | Mokaya et al. | |
| 2015/0106025 | A1 | 4/2015 | Keller et al. | |
| 2015/0272482 | A1 | 10/2015 | Houmanfar et al. | |
| 2016/0027325 | A1 | 1/2016 | Malhotra | |
| 2016/0313801 | A1* | 10/2016 | Wagner | G06F 1/163 |
| 2017/0135640 | A1 | 5/2017 | Gunasekar et al. | |
| 2017/0186335 | A1 | 6/2017 | Matsunaga | |
| 2017/0224985 | A1 | 8/2017 | Debur et al. | |
| 2018/0024635 | A1 | 1/2018 | Kaifosh et al. | |
| 2018/0047157 | A1 | 2/2018 | Sinha et al. | |
| 2018/0121713 | A1 | 5/2018 | Guo et al. | |
| 2019/0046067 | A1 | 2/2019 | Du et al. | |
| 2019/0343459 | A1 | 11/2019 | Korzinov et al. | |
| 2020/0054931 | A1 | 2/2020 | Martin et al. | |
| 2020/0155018 | A1 | 5/2020 | Igami | |
| 2020/0302236 | A1 | 9/2020 | Gao et al. | |
| 2020/0310541 | A1 | 10/2020 | Reisman et al. | |
| 2020/0401224 | A1 | 12/2020 | Cotton | |

FOREIGN PATENT DOCUMENTS

| | | | |
|---|---|---|---|
| CN | 104720787 | A | 6/2015 |
| CN | 104720821 | A | 6/2015 |
| CN | 105635669 | A | 6/2016 |
| CN | 105796112 | A | 7/2016 |
| CN | 105797350 | A | 7/2016 |
| CN | 105997064 | A | 10/2016 |
| CN | 106073793 | A | 11/2016 |
| CN | 107115114 | A | 9/2017 |
| CN | 107320095 | A | 11/2017 |
| CN | 107349594 | A | 11/2017 |
| CN | 107361773 | A | 11/2017 |
| CN | 207071088 | U | 3/2018 |
| CN | 108143409 | A | 6/2018 |
| CN | 108209910 | A | 6/2018 |
| CN | 108211308 | A | 6/2018 |
| CN | 108211309 | A | 6/2018 |
| CN | 108211310 | A | 6/2018 |
| CN | 108566520 | A | 9/2018 |
| CN | 105997064 | B | 10/2018 |
| CN | 108983954 | A | 12/2018 |
| CN | 109068081 | A | 12/2018 |
| CN | 109191588 | A | 1/2019 |
| CN | 109330609 | A | 2/2019 |
| CN | 110109532 | A | 8/2019 |
| CN | 110327048 | A | 10/2019 |
| CN | 110443309 | A | 11/2019 |
| CN | 110472611 | A | 11/2019 |
| CN | 110478883 | A | 11/2019 |
| CN | 110569775 | A | 12/2019 |
| CN | 110609621 | A | 12/2019 |
| CN | 110638444 | A | 1/2020 |
| CN | 111028317 | A | 4/2020 |
| CN | 111317446 | A | 6/2020 |
| CN | 111561352 | | 8/2020 |
| CN | 111684793 | | 9/2020 |
| CN | 111707307 | | 9/2020 |
| CN | 111713426 | | 9/2020 |
| CN | 111803061 | A | 10/2020 |
| CN | 111938656 | A | 11/2020 |
| CN | 108143409 | B | 1/2021 |
| CN | 112214109 | A | 1/2021 |
| CN | 112472042 | A | 3/2021 |
| JP | 2003339908 | A | 12/2003 |
| JP | 2010246636 | A | 11/2010 |
| JP | 2011103914 | A | 6/2011 |
| JP | 2012024521 | A | 2/2012 |
| JP | 3181442 | U | 2/2013 |
| JP | 2014002655 | A | 1/2014 |
| JP | 2019030520 | A | 2/2019 |
| JP | 2020103653 | A | 7/2020 |
| JP | 2020155961 | A | 9/2020 |
| KR | 20180086547 | | 8/2018 |
| RU | 2551193 | C1 | 5/2015 |
| WO | 2018214522 | A1 | 11/2018 |
| WO | 2020096553 | | 5/2020 |

OTHER PUBLICATIONS

Office Action in Russian Application No. 2022121115 mailed on Mar. 16, 2023, 22 pages.
Notice of Rejection in Japanese Application No. 2022-560093 mailed on Oct. 2, 2023, 8 pages.
The Extended European Search Report in European Application No. 22743434.7 mailed on Jul. 19, 2023, 8 pages.
International Search Report in PCT/CN2022/074377 mailed on Apr. 11, 2022, 5 pages.
Written Opinion in PCT/CN2022/074377 mailed on Apr. 11, 2022, 6 pages.
International Search Report in PCT/CN2021/081931 mailed on Dec. 22, 2021, 8 pages.
Written Opinion in PCT/CN2021/081931 mailed on Dec. 22, 2021, 8 pages.
First Office Action in Brazilian Application No. 112022016523-4 mailed on Sep. 9, 2025, 8 pages.

(56) References Cited

OTHER PUBLICATIONS

João Lopes et al., Hand/arm gesture segmentation by motion using IMU and EMG sensing, 27th International Conference on Flexible Automation and Intelligent Manufacturing, 11: 107-113, 2017.

Notice of Reasons for Rejection in Japanese Application No. 2023528497 mailed on May 7, 2024, 12 pages.

* cited by examiner

400

MOTION DATA PROCESSING METHOD AND MOTION MONITORING SYSTEM

CROSS-REFERENCE TO RELATED APPLICATIONS

This application is a continuation of International Application No. PCT/CN2022/074377, filed on Jan. 27, 2022, which claims priority to International Patent Application No. PCT/CN2021/081931, filed on Mar. 19, 2021, the contents of which are hereby incorporated by reference.

TECHNICAL FIELD

The present disclosure relates to the field of a wearable device, and in particular, to a motion data processing method and a motion monitoring system.

BACKGROUND

With the attention of scientific motion and physical health, a motion monitoring device is greatly developing. At present, the motion monitoring device mainly monitors physiological parameter information (e.g., an electromyography (EMG) signal) during a motion of a user, displays physiological data to the user, and gives a suggestion based on the physiological data. In order to help a user exercise more scientifically and more effectively, the motion monitoring device needs to have the function of displaying the strength of each muscle (that is, the amplitude of the EMG signal) to the user in real-time. In order to give the user a better experience, the motion monitoring device needs to smooth the EMG signal to obtain a smooth EMG energy map. In the prior art, the motion monitoring device cannot identify an abnormal signal when an EMG signal is processed, such as an abnormal EMG signal caused by improper clothing, pulling, a motion artifact, etc., so that the EMG energy map is unstable and the user experience is poor.

Therefore, it is desirable to provide a motion data processing method and a motion monitoring system for identifying and correcting an abnormal signal in real-time.

SUMMARY

The present disclosure may provide a motion data processing method and a motion monitoring system for identifying and correcting an abnormal signal in real-time.

According to a first aspect of the present disclosure, a motion data processing method may be provided. The motion data processing method may include: obtaining, in real-time, an electromyography (EMG) signal corresponding to a measurement position during a motion of a user; determining, based on the EMG signal, an abnormal signal in the EMG signal; and correcting the abnormal signal.

In some embodiments, the determining, based on the EMG signal, an abnormal signal in the EMG signal may include: processing the EMG signal in a time domain to determine the abnormal signal; or processing the EMG signal in a frequency domain to determine the abnormal signal.

In some embodiments, the processing the EMG signal in a time domain to determine the abnormal signal may include: selecting, based on a time domain window of the EMG signal, at least one time window from the time domain window of the EMG signal, wherein each of the at least one time window covers a different time range; and determining, based on feature information corresponding to the EMG signal in the at least one time window, the abnormal signal.

In some embodiments, the feature information may include at least one of amplitude information or statistical information of the amplitude information. The statistical information of the amplitude information may include at least one of an entropy, a variance, a standard deviation, a standard deviation of the standard deviation, or a zero-crossing rate of the amplitude information.

In some embodiments, the abnormal signal may include an abrupt signal. The at least one time window may include a plurality of time windows, and the determining, based on feature information corresponding to the EMG signal in the at least one time window, the abnormal signal may include: determining feature information corresponding to the EMG signal in the plurality of time windows; and determining that a ratio of feature information corresponding to a time window subsequent to a time range to feature information corresponding to a time window previous to the time range exceeds a predetermined first threshold, and designating the EMG signal in the time window subsequent to the time range as the abrupt signal.

In some embodiments, the abnormal signal may include a missing signal, and the determining, based on feature information corresponding to the EMG signal in the at least one time window, the abnormal signal may include: determining at least one piece of feature information corresponding to the EMG signal in the at least one time window; and designating the EMG signal in a time window corresponding to feature information that is in the at least one piece of feature information and lower than prestored feature information of a second threshold as the missing signal.

In some embodiments, the abnormal signal may include a saturation signal, and the determining, based on feature information corresponding to the EMG signal in the at least one time window, the abnormal signal may include: determining at least one piece of feature information corresponding to the EMG signal in the at least one time window; and designating the EMG signal in a time window corresponding to feature information that is in the at least one piece of feature information and exceeds prestored saturation feature information as the saturation signal.

In some embodiments, the EMG signal may include a signal obtained based on a direct current (DC) removing algorithm. The DC removing algorithm may include at least one of a de-averaging algorithm or a high-pass filtering algorithm.

In some embodiments, the abnormal signal may further include an oscillation signal caused by the high-pass filtering algorithm. The processing the EMG signal in a time domain to determine the abnormal signal may include: determining a reference oscillation height and a reference duration of the oscillation signal based on a filter parameter of the high-pass filtering algorithm; and matching the EMG signal with the reference oscillation height and the reference duration in real-time; and designating the EMG signal corresponding to a signal interval within which the EMG signal matches the reference oscillation height and the reference duration as the oscillation signal.

In some embodiments, the processing the EMG signal in a frequency domain to determine the abnormal signal may include: obtaining, based on a frequency domain conversion algorithm, a frequency domain signal of the EMG signal in the frequency domain in real-time; determining a spectral feature of the frequency domain signal in real-time; and determining the EMG signal corresponding to the frequency domain signal whose spectral feature fails to meet a predetermined condition as the abnormal signal.

In some embodiments, the spectral feature may include at least one of a spectral shape, a power spectral density, a mean power frequency, a median frequency, or wavelet scale.

In some embodiments, the correcting the abnormal signal may include: performing, in real-time, a data sampling operation on the EMG signal before the abnormal signal to obtain sampling data; determining, based on the sampling data corresponding to a time domain window of the EMG signal, prediction data corresponding to a time point when the abnormal signal appears; determining, based on the prediction data, correction data corresponding to the time point when the abnormal signal appears; and correcting the abnormal signal by using the correction data.

In some embodiments, the determining, based on the sampling data corresponding to a time domain window of the EMG signal, prediction data corresponding to a time point when the abnormal signal appears may include at least one of: determining, based on the sampling data corresponding to the time domain window, a fitting function; determining, based on the fitting function, the prediction data corresponding to the time point when the abnormal signal appears; or determining, based on the sampling data corresponding to the time domain window and a trained long-short term memory (LSTM) network, the prediction data corresponding to the time point when the abnormal signal appears.

In some embodiments, the determining, based on the prediction data, correction data corresponding to a time point when the abnormal signal appears may include: in response to determining that the prediction data is within a predetermined range, designating the prediction data as the correction data, wherein the predetermined range includes a data range formed by a maximum value and a minimum value of the EMG signal in the time domain window; or in response to determining that the prediction data is out of the predetermined range, designating sampling data corresponding to the EMG signal adjacent to the abnormal signal within at least one frame as the correction data.

According to a second aspect of the present disclosure, a motion monitoring system may be provided. The motion monitoring system may include at least one storage medium and at least one processor. The at least one storage medium may store at least one instruction set for motion data processing. The at least one processor may be in communication with the at least one storage medium. When the motion monitoring system is operated, the at least one processor reads the at least one instruction set and implements the motion data processing method of the first aspect of the present disclosure.

It could be seen from the above technical scheme that the motion data processing method and motion monitoring system provided by the present disclosure may process the EMG signal from the frequency domain or time domain to identify the abnormal signal in the EMG signal, such as an abrupt signal, a missing signal, a saturation signal, and an oscillation signal caused by the high-pass filtering algorithm, etc. The motion data processing method and motion monitoring system may further perform a data sampling operation on the EMG signal through a data sampling algorithm, predict data corresponding to the time point when the abnormal signal appears based on the sampling data, so as to obtain the prediction data, and replace the abnormal signal by using the prediction data to correct the abnormal signal. The motion data processing method and motion monitoring system may not only accurately identify the abnormal signal, but further correct the abnormal signal, so that the corrected data can be more in line with an actual motion of a user, thereby improving user experience. The motion data processing method and motion monitoring system may further remind the user that a device is wearing abnormally in time when an abnormal signal is identified, thereby making the data collection more accurate.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
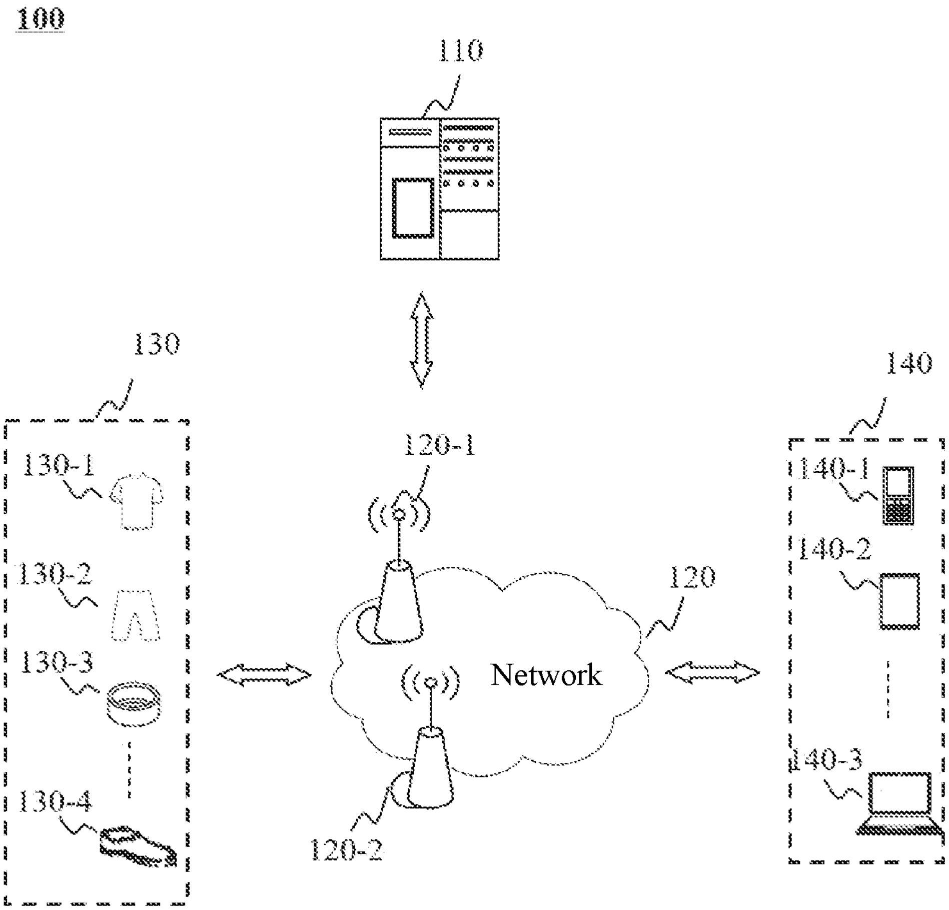
FIG. 1 is a schematic diagram illustrating an exemplary application scenario of a motion monitoring system according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that the system implements according to the embodiment of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

A motion monitoring system may be provided in the present disclosure. The motion monitoring system may obtain an action signal during a motion of a user. The action signal may include an electromyography (EMG) signal, an attitude signal, an electrocardiogram (ECG) signal, a respiratory frequency signal, or the like, or any combination thereof. The motion monitoring system may monitor an action of a motion of the user at least based on feature information corresponding to the EMG signal or feature information corresponding to the attitude signal. An action type, an action count, an action quality, an action time, or physiological parameter information when the user performs an action may be determined by frequency information, amplitude information, etc., corresponding to the EMG signal, an angular velocity, an angular velocity direction, an angular velocity value of the angular velocity, an angle, displacement information, stress, etc., corresponding to the attitude signal. In some embodiments, the motion monitoring system may also generate feedback on a fitness action of the user based on an analysis result of the fitness action of the user, to guide the user's fitness. For example, when the fitness action of the user is not standard, the motion monitoring system may send prompt information (e.g., a voice prompt, a vibration prompt, a current stimulation, etc.) to the user. The motion monitoring system may be applied to a wearable device (e.g., clothing, a bracelet, a helmet), a medical testing device (e.g., an EMG tester), a fitness device, etc. The motion monitoring system may accurately monitor and give feedback on the user's action by obtaining the action signal during a motion of the user, without participation of professionals, which may improve the fitness efficiency of the user and reduce the fitness cost of the user.

FIG. 1 is a schematic diagram illustrating an exemplary application scenario of a motion monitoring system according to some embodiments of the present disclosure. As shown in FIG. 1, the motion monitoring system 100 may include a processing device 110, a network 120, a wearable device 130, and a mobile terminal device 140. The motion monitoring system 100 may obtain an action signal (e.g., an electromyography (EMG) signal, an attitude signal, an electrocardiogram (ECG) signal, a respiratory frequency signal, etc.) representing an action of a motion of the user. The motion monitoring system 100 may monitor and give feedback on the action during the motion of the user based on the action signal.

For example, the motion monitoring system 100 may monitor and give feedback on the user's action during fitness. When the user wears the wearable device 130 for fitness, the wearable device 130 may obtain the action signal of the user. The processing device 110 or the mobile terminal device 140 may receive and analyze the action signal of the user to determine whether the fitness action of the user is standardized, so as to monitor the user's action. Specifically, the monitoring the user's action may include monitoring an action type, an action count, an action quality, an action time, or physiological parameter information when the user performs the action. Furthermore, the motion monitoring system 100 may generate feedback on the fitness action of the user based on an analysis result of the fitness action of the user, to guide the users' fitness.

As another example, the motion monitoring system 100 may monitor and give feedback on an action of the user when running. For example, when the user wears the wearable device 130 for running, the motion monitoring system 100 may monitor whether a running action of the user is standardized, whether a running time meets a health standard, or the like. When the running time of the user is too long or the running action of the user is incorrect, the wearable device 130 may feedback the motion state to the user to prompt the user that the running action or the running time needs to be adjusted.

In some embodiments, the processing device 110 may be configured to process information and/or data related to the motion of the user. For example, the processing device 110 may receive an action signal of the user (e.g., an EMG signal, an attitude signal, an ECG signal, a respiratory frequency signal, etc.), and feature information corresponding to the action signal (e.g., feature information corresponding to the EMG signal and feature information corresponding to the attitude signal in the action signal) may further be extracted. In some embodiments, the processing device 110 may perform a specific signal processing, such as a signal segmentation, a signal pre-processing (e.g., signal correction processing, filtering processing, etc.) on the EMG signal or the attitude signal collected by the wearable device 130. In some embodiments, the processing device 110 may also determine whether the user's action is correct based on the action signal of the user. For example, the processing device 110 may determine whether the user's action is correct based on the feature information (e.g., amplitude information, frequency information, etc.) corresponding to the EMG signal. As another example, the processing device 110 may determine whether the user's action is correct based on the feature information (e.g., an angular velocity, an angular velocity direction, an accelerated velocity of the angular velocity, an angle, displacement information, stress, etc.) corresponding to the attitude signal. As another example, the processing device 110 may determine whether the user's action is correct based on the feature information corresponding to the EMG signal and the feature information corresponding to the attitude signal. In some embodiments, the processing device 110 may also determine whether the physiological parameter information during the motion of the user meets a health standard. In some embodiments, the processing device 110 may also send an instruction to give feedback on the motion of the user. For example, when the user is running, the motion monitoring system 100 may monitor that the user's running time is too long. At this time, the processing device 110 may send an instruction to the mobile terminal device 140 to prompt the user to adjust the running time. It should be noted that the feature information corresponding to the attitude signal may be not limited to the angular velocity, the angular velocity direction, the accelerated velocity of the angular velocity, the angle, the displacement information, the stress, etc., and may also be other feature information. Any parameter information that is configured to reflect a relative motion of the user's body may be feature information corresponding to the attitude signal. For example, when an attitude sensor is a strain gauge sensor, a bending angle and a bending direction of the user's joint may be obtained by measuring a magnitude of the resistance in the strain gauge sensor that changes with the stretch length.

In some embodiments, the processing device 110 may be local or remote. For example, the processing device 110 may access information and/or information stored in the wearable device 130 and/or the mobile terminal device 140 via the network 120. In some embodiments, the processing device 110 may be directly connected to the wearable device 130, and/or the mobile terminal device 140 to access the stored information and/or data. For example, the processing device 110 may be located in the wearable device 130, and realize information interaction with the mobile terminal device 140 via the network 120. As another example, the processing device 110 may be located in the mobile terminal device 140 and realize information interaction with the wearable device 130 via the network. In some embodiments, the processing device 110 may be implemented on a cloud platform.

In some embodiments, the processing device 110 may process data and/or information related to motion monitoring to implement the one or more functions described in present disclosure. In some embodiments, the processing device 110 may obtain an action signal collected by the wearable device 130 during a motion of a user. In some embodiments, the processing device 110 may send a control instruction to the wearable device 130 or the mobile terminal device 140. The control instruction may control the wearable device 130 and a sensor thereof to be turned on or off, and may also control the mobile terminal device 140 to send prompt information. In some embodiments, the processing device 110 may include one or more sub-processing devices (e.g., a single-core processing device or a multi-core-multi-chip processing device).

The network 120 may facilitate exchange of data and/or information in the motion monitoring system 100. In some embodiments, one or more components of the motion monitoring system 100 may transmit data and/or information to other component(s) of the motion monitoring system 100 via the network 120. For example, the action signal collected by the wearable device 130 may be transmitted to the processing device 110 via the network 120. As another example, a confirmation result of the action signal in the processing device 110 may be transmitted to the mobile terminal device 140 via the network 120. In some embodiments, the network 120 may be any type of a wired or wireless network, or combination thereof.

The wearable device 130 may refer to clothing or a device with a wearable function. In some embodiments, the wearable device 130 may include but be not limited to a top device 130-1, a pants device 130-2, a bracelet device 130-3, a shoe 130-4, etc. In some embodiments, the wearable device 130 may include a plurality of sensors. The sensors may obtain various action signals (e.g., an EMG signal, an attitude signal, temperature information, a heartbeat frequency, an ECG signal, etc.) during a motion of a user. In some embodiments, the sensor may include but be not limited to an EMG sensor, an attitude sensor, a temperature sensor, a humidity sensor, an ECG sensor, a blood oxygen saturation sensor, a Hall sensor, an electrical skin sensor, a rotation sensor, or the like, or any combination thereof. For example, the EMG sensor may be provided at a muscle position (e.g., a bicep, a tricep, a latissimus dorsum, a trapezius, etc.) of a human body in the top device 130-1. The EMG sensor may fit the user's skin and collect the EMG signal during the motion of the user. As another example, the ECG sensor may be provided near a left pectoral muscle of a human body in the top device 130-1. The ECG sensor may collect the ECG signal of the user. As another example, the attitude sensor may be provided at a muscle position (e.g., a gluteus maximus, a vastus lateralis, a vastus medialis, a gastrocnemius, etc.) of a human body. The attitude sensor may collect the attitude signal of the user. In some embodiments, the wearable device 130 may also give feedback on the users' action. For example, when the action of a certain part of the body during a motion does not meet a standard, the EMG sensor corresponding to the part may generate a stimulation signal (e.g., a current stimulation or a hitting signal) to remind the user.

It should be noted that the wearable device 130 is not limited to the top device 130-1, the pants device 130-2, the bracelet device 130-3, and the shoe device 130-4 shown in FIG. 1, and may also include other devices applied to a device that need to be monitored, such as a helmet device, a kneelet device, etc., which is not limited herein. Any device that may use the motion monitoring method contained in the present disclosure is within the scope of protection of the present disclosure.

In some embodiments, the mobile terminal device 140 may obtain information or data from the motion monitoring system 100. In some embodiments, the mobile terminal device 140 may receive motion data processed by the processing device 110, and a motion record may be fed back based on the processed motion data, or the like. Exemplary feedback manners may include but be not limited to a voice prompt, an image prompt, a video display, a text prompt, etc. In some embodiments, the user may obtain an action record during a motion of the user through the mobile terminal device 140. For example, the mobile terminal device 140 may be connected (e.g., wired connected or wireless connected) with the wearable device 130 via the network 120.

The user may obtain an action record during the motion of the user based on the mobile terminal device 140. The action record may be transmitted to the processing device 110 through the mobile terminal device 140. In some embodiments, the mobile terminal device 140 may include a mobile device 140-1, a tablet computer 140-2, a laptop computer 140-3, or the like, or any combination thereof. In some embodiments, the mobile device 140-1 may include a mobile phone, a smart home device, a smart mobile device, a virtual reality device, an augmented reality device, or the like, or any combination thereof. In some embodiments, the smart home device may include a control device of an intelligent electrical apparatus, a smart monitoring device, a smart television, a smart video camera, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof.

In some embodiments, the motion monitoring system 100 may also include a database. The database may store data (e.g., an initially set threshold condition, etc.) and/or an instruction (e.g., a feedback instruction). In some embodiments, the database may store data obtained from the wearable device 130 and/or the mobile terminal device 140. In some embodiments, the database may store information and/or instructions for execution or usage by the processing device 110 to perform the exemplary methods described in the present disclosure. In some embodiments, the database may be connected to the network 120 to communicate with one or more components (e.g., the processing device 110, the wearable device 130, the mobile terminal device 140, etc.) of the motion monitoring system 100. The one or more components of the motion monitoring system 100 may access the data or instructions stored in the database via the network 120. In some embodiments, the database may directly connect or communicate with the one or more components in the motion monitoring system 100. In some embodiments, the database may be part of the processing device 110.

Figure 2:
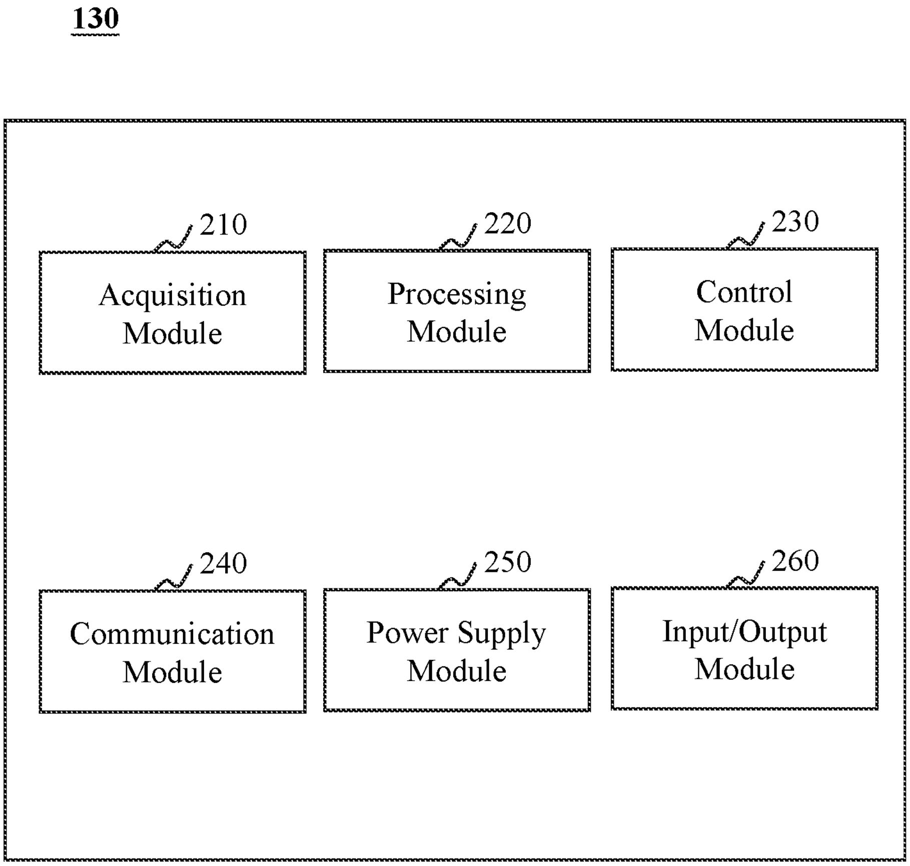
FIG. 2 is a schematic diagram illustrating exemplary hardware and/or software components of an exemplary wearable device according to some embodiments of the present disclosure.

FIG. 2 is a schematic diagram illustrating exemplary hardware and/or software components of an exemplary wearable device 130 according to some embodiments of the present disclosure. As shown in FIG. 2, the wearable device 130 may include an acquisition module 210, a processing module 220 (also referred to as a processor), a control module 230 (also referred to as a main control, a micro controller unit (MCU), a controller), a communication module 240, a power supply module 250, and an input/output module 260.

The acquisition module 210 may be configured to obtain an action signal during a motion of a user. In some embodiments, the acquisition module 210 may include a sensor unit. The sensor unit may be configured to obtain one or more action signals during the motion of the user. In some embodiments, the sensor unit may include but be not limited, an EMG sensor, an attitude sensor, an ECG sensor, a respiration sensor, a temperature sensor, a humidity sensor, an inertial sensor, a blood oxygen saturation sensor, a Hall sensor, an electrical skin sensor, a rotation sensor, or the like, or any combination thereof. In some embodiments, the action signal may include an EMG signal, an attitude signal, an ECG signal, a respiratory frequency, a temperature signal, a humidity signal, or the like, or any combination thereof. The sensor unit may be placed in different positions of the wearable device 130 based on a type of the action signal. For example, in some embodiments, the EMG sensor (also referred to as an electrode component) may be disposed at the muscle position of the human body, and the EMG sensor may be configured to collect the EMG signal during the motion of the user. The EMG signal and feature information corresponding to the EMG signal (e.g., frequency information, amplitude information, etc.) may reflect the state of the muscle during the motion of the user. The attitude sensor may be disposed at different positions (e.g., positions in the wearable device 130 corresponding to a torso, a limb, and a joint) of the human body, and the attitude sensor may be configured to collect the attitude signal during the motion of the user. The attitude signal and feature information (e.g., an angular velocity direction, an angular velocity value, an accelerated velocity of the angular velocity, an angle, displacement information, stress, etc.) corresponding to the attitude signal may reflect the posture of the motion of the user. The ECG sensor may be disposed at a position around the chest of the human body. The ECG sensor may be configured to collect ECG data during the motion of the user. The respiration sensor may be disposed at a position around the chest of the human body. The respiration sensor may be configured to collect respiration data (e.g., a respiratory frequency, a respiratory amplitude, etc.) during the motion of the user. The temperature sensor may be configured to collect temperature data (e.g., a body surface temperature) during the motion of the user. The humidity sensor may be configured to collect humidity data of an external environment during the motion of the user.

The processing module 220 may process data from the acquisition module 210, the control module 230, the communication module 240, the power supply module 250 and/or the input/output module 260. For example, the processing module 220 may process the action signal from the acquisition module 210 during the motion of the user. In some embodiments, the processing module 220 may perform pre-processing on the action signal (e.g., an EMG signal and an attitude signal) obtained by the acquisition module 210. For example, the processing module 220 may perform segmentation processing on the EMG signal or the attitude signal during the motion of the user. As another example, the processing module 220 may perform pre-processing (e.g., filtering processing and signal correction processing) on the EMG signal during the motion of the user, so as to improve quality of the EMG signal. As another example, the processing module 220 may determine feature information corresponding to the attitude signal based on the attitude signal during the motion of the user. In some embodiments, the processing module 220 may process an instruction or an operation from the input/output module 260. In some embodiments, the processed data may be stored in a storage or a hard disk. In some embodiments, the processing module 220 may transmit the processed data through the communication module 240 or the network 120 to one or more components in the motion monitoring system 100. For example, the processing module 220 may send a monitoring result of the motion of the user to the control module 230, and the control module 230 may execute a subsequent operation or instruction based on the action determination result.

The control module 230 may be connected to other modules in the wearable device 130. In some embodiments, the control module 230 may control a running state of other modules in the wearable device 130. For example, the control module 230 may control a power supply state (e.g., a normal mode, a power-saving mode), a power supply time, etc., of the power supply module 250. As another example, the control module 230 may control the input/output module 260 based on the action determination result of the user, and then may control the mobile terminal device 140 to send a feedback result of the motion of the user. When there is a problem with the action during the motion of the user (e.g., the action does not meet a standard), the control module 230 may control the input/output module 260, and then may control the mobile terminal device 140 to give feedback to the user, so that the user may know his/her own motion status in real-time and adjust the action. In some embodiments, the control module 230 may also control one or more sensors or other modules in the acquisition module 210 to give feedback to the human body. For example, when the strength of a certain piece of muscle during the motion of the user is too large, the control module 230 may control an electrode module at the muscle position to electrically stimulate the user to prompt the user to adjust the action in time.

In some embodiments, the communication module 240 may be configured to exchange of information or data. In some embodiments, the communication module 240 may be configured for communication between internal components of the wearable device 130. For example, the acquisition module 210 may send a user action signal (e.g., an EMG signal, an attitude signal, etc.) to the communication module 240, and the communication module 240 may send the action signal to the processing module 220. In some embodiments, the communication module 240 may also be configured for communication between the wearable device 130 and other components in the motion monitoring system 100. For example, the communication module 240 may send state information (e.g., a switch state) of the wearable device 130 to the processing device 110, and the processing device 110 may monitor the wearable device 130 based on the state information. The communication module 240 may use a wired technology, a wireless technology, or a wired/wireless hybrid technology.

In some embodiments, the power supply module 250 may provide power to other components in the motion monitoring system 100.

The input/output module 260 may obtain, transmit, and send a signal. The input/output module 260 may connect or communicate with other components in the motion monitoring system 100. The other components in the motion monitoring system 100 may be connected or communicated through the input/output module 260.

It should be noted that the above descriptions of the motion monitoring system 100 and modules are merely for convenience of descriptions, and may not limit one or more embodiments of the present disclosure to the scope of the embodiments. For those skilled in the art, after understanding the principle of the present disclosure, it is possible to combine the modules in various ways, form a sub-system to connect with other modules without departing from the principle, or omit the one or more modules. For example, the acquisition module 210 and the processing module 220 may be a single module. The single module may implement functions of obtaining and processing the action signal of the user. As another example, the processing module 220 may be not disposed in the wearable device 130, but integrated in the processing device 110. All such modifications are within the scope of the one or more embodiments of the present disclosure.

Figure 3:
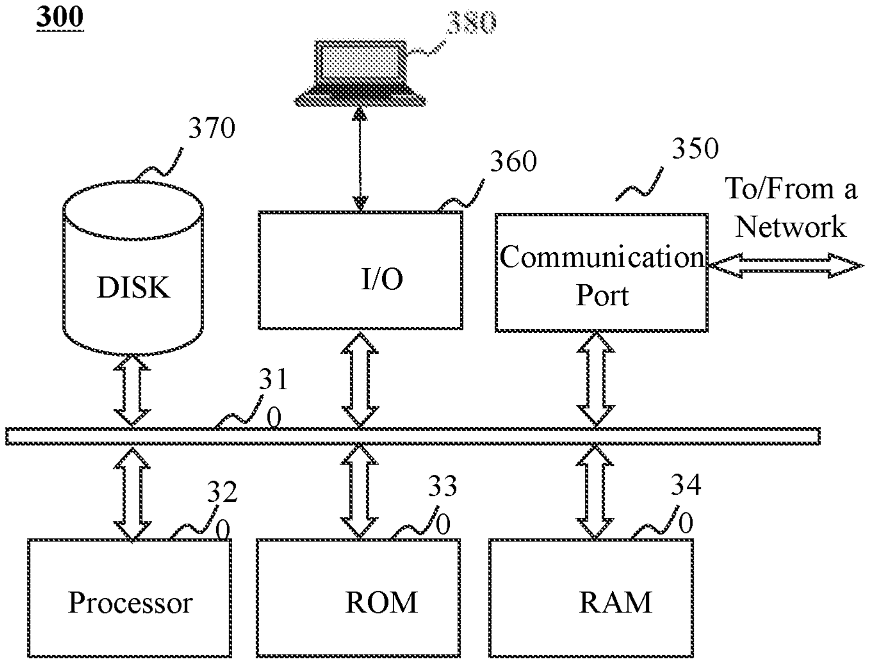
FIG. 3 is a schematic diagram illustrating exemplary hardware and/or software components of an exemplary computing device according to some embodiments of the present disclosure.

FIG. 3 is a schematic diagram illustrating exemplary hardware and/or software components of an exemplary computing device 300 according to some embodiments of the present disclosure. In some embodiments, the processing device 110 and/or the mobile terminal device 140 may be arranged on the computing device 300. As shown in FIG. 3, the computing device 300 may include an internal communication bus 310, a processor 320, a read-only memory (ROM) 330, a random access memory (RAM) 340, a communication port 350, an input/output interface 360, a disk 370, and a user interface 380.

The internal communication bus 310 may realize data communication among components in the computing device 300. For example, the processor 320 may send data to a storage or other hardware such as the input/output interface 360 through the internal communication bus 310.

The processor 320 may execute computer instructions (e.g., program codes) and perform functions of the motion monitoring system 100 described in the present disclosure. The computer instructions may include, for example, programs, objects, components, data structures, procedures, modules, and functions, which perform particular functions described herein. For example, the processor 320 may process an action signal (e.g., an EMG signal, an attitude signal) obtained from the wearable device 130 or/and the mobile terminal device 140 from the motion monitoring system 100, and monitor the action of the motion of the user based on the action signal during the motion of the user. Merely for illustration purposes, only one processor is described in the computing device in FIG. 3. However, it should be noted that the computing device 300 in the present disclosure may also include a plurality of processors.

The storage of the computing device 300 (e.g., the read-only memory (ROM) 330, the random access memory (RAM) 340, the disk 370, etc.) may store data/information obtained from any other components of the motion monitoring system 100. In some embodiments, the storage of the computing device 300 may be located in the wearable device 130 or in the processing device 110. The storage may also include at least one set of instructions stored in the storage. The instructions may be computer programs. The computer programs may be configured to perform functions of the motion monitoring system 100 of the present disclosure. the computer programs may include, for example, programs, routines, objects, components, data structures, procedures, modules, etc., of the motion data processing method provided in the present disclosure.

The input/output interface 360 may be configured to input or output signals, data or information. In some embodiments, the input/output interface 360 may enable a user interaction with the motion monitoring system 100.

The disk 370 may be configured to store information and data generated by or received from the processing device. For example, the disk 370 may store user confirmation information of the user. In some embodiments, the disk 370 may be disposed in the processing device 110 or in the wearable device 130. The user interface 380 may realize interaction and information exchange between the computing device 300 and a user. In some embodiments, the user interface 380 may be configured to present a motion record generated by the motion monitoring system 100 to the user. In some embodiments, the user interface 380 may include a physical display, such as a display with a speaker, a liquid crystal display (LCD), a light-emitting diode (LED)-based display, an organic light-emitting diode (OLED) display, an electronic ink display (E-Ink), etc.

Figure 4:
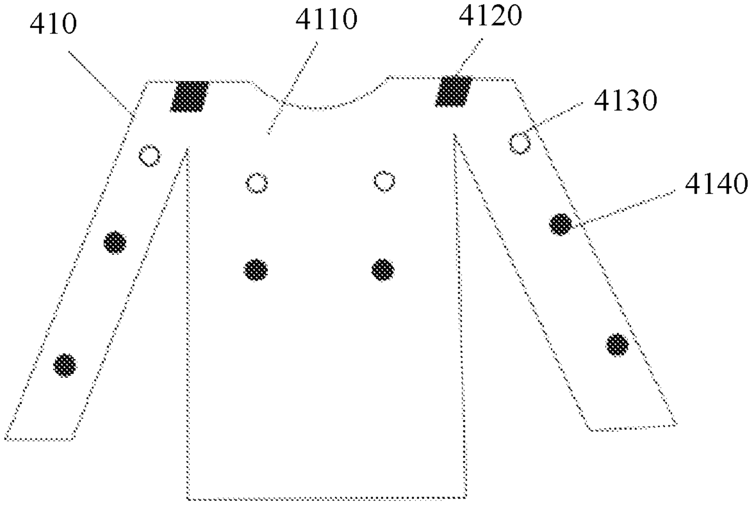
FIG. 4 is a structural diagram illustrating an exemplary wearable device according to some embodiments of the present disclosure.

FIG. 4 is a structural diagram illustrating an exemplary wearable device according to some embodiments of the present disclosure. In order to further describe the wearable device, an upper garment is used as an exemplary illustration. As shown in FIG. 4, the wearable device 400 may include an upper garment 410. The upper garment 410 may include an upper garment base 4110, at least one upper garment processing module 4120, at least one upper garment feedback module 4130, at least one upper garment acquisition module 4140, etc. The upper garment base 4110 may be clothing worn on the upper body of the human body. In some embodiments, the upper garment base 4110 may include a short-sleeved T-shirt, a long-sleeved T-shirt, a shirt, an outerwear, etc. The at least one upper garment processing module 4120 and the at least one upper garment acquisition module 4140 may be located in areas of the upper garment base 4110 that fit with different parts of the human body. The at least one upper garment feedback module 4130 may be located at any position of the upper garment base 4110. The at least one upper garment feedback module 4130 may be configured to give feedback on motion state information of the upper body of the user. Feedback manners may include but be not limited, a voice prompt, a text prompt, a pressure prompt, a current stimulation, etc. In some embodiments, the at least one upper garment acquisition module 4140 may include but be not limited to an attitude sensor, an ECG sensor, an EMG sensor, a temperature sensor, a humidity sensor, an inertial sensor, an acid-base sensor, a sound wave transducer, or the like, or any combination thereof. The sensor in the upper garment acquisition module 4140 may be placed in different positions of the user's body based on different signals. For example, when the attitude sensor is configured to obtain an attitude signal during the motion of the user, the attitude sensor may be placed in a position corresponding to a human torso, an arm, and a joint in the upper garment base 4110. As another example, when the EMG sensor is configured to obtain an EMG signal during the motion of the user, the EMG sensor may be located near the muscle of the user. In some embodiments, the attitude sensor may include but be not limited, an acceleration triaxial sensor, an angular velocity triaxial sensor, a magnetic force sensor, or the like, or any combination thereof. For example, the attitude sensor may include the acceleration triaxial sensor and the angular velocity triaxial sensor. In some embodiments, the attitude sensor may also include a strain gauge sensor. The strain gauge sensor may refer to a sensor that may be based on the strain generated by a deformation of a subject in response to a force. In some embodiments, the strain gauge sensor may include but be not limited to a strain-gauge-type load cell, a strain-gauge-type pressure sensor, a strain-gauge-type torque sensor, a strain-gauge-type displacement sensor, a strain-gauge-type acceleration sensor, or the like, or any combination thereof. For example, the strain gauge sensor may be disposed at the joint position of the user. A bending angle and a bending direction of the user's joint may be obtained by measuring a magnitude of the resistance in the strain gauge sensor that changes with the stretch length. It should be noted that in addition to the above-mentioned upper garment base 4110, the upper garment processing module 4120, the upper garment feedback module 4130, and the upper garment acquisition module 4140, the upper garment 410 may also include other modules, such as a power supply module, a communication module, an input/output module, etc. The upper garment processing module 4120 may be similar to the processing module 220 in FIG. 2. The upper garment acquisition module 4140 may be similar to the acquisition module 210 in FIG. 2. The detailed descriptions for each module in upper garment 410 may refer to the descriptions in FIG. 2, which may be not described herein.

Figure 5:
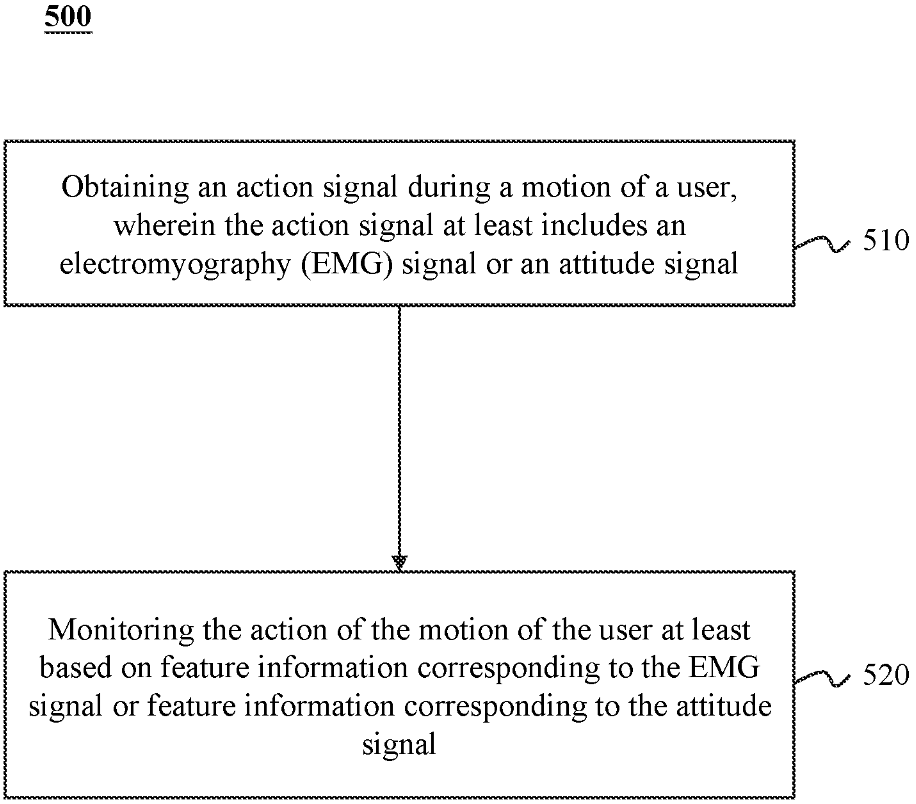
FIG. 5 is a flowchart illustrating an exemplary process for motion monitoring according to some embodiments of the present disclosure.

FIG. 5 is a flowchart illustrating an exemplary process for motion monitoring according to some embodiments of the present disclosure. As shown in FIG. 5, the process 500 may include following operations.

In 510, an action signal during a motion of a user may be obtained.

In some embodiments, operation 510 may be performed by the acquisition module 210. An action signal may refer to human body parameter information during a motion of a user. In some embodiments, the human body parameter information may include but be not limited to an EMG signal, an attitude signal, an ECG signal, a temperature signal, a humidity signal, a blood oxygen concentration, a respiratory frequency, or the like, or any combination thereof. In some embodiments, an EMG sensor in the acquisition module 210 may collect the EMG signal during a motion of a user. For example, when the user clamps the chest in a sitting position, the EMG sensor corresponding to a position of a pectoral muscle, a latissimus dorsum, etc., of the human body in the wearable device may collect an EMG signal of a corresponding muscle position of the user. As another example, when the user squats, the EMG sensor corresponding to a position of a gluteus maximus, a quadricep, etc., of the human body in the wearable device may collect an EMG signal of a corresponding muscle position of the user. As another example, when the user is running, the EMG sensor corresponding to a position of a gastrocnemius, etc., of the human body in the wearable device may collect an EMG signal of the position of the gastrocnemius, etc., of the human body. In some embodiments, the attitude sensor in the acquisition module 210 may collect an attitude signal during the motion of the user. For example, when the user performs a barbell bench press motion, the attitude sensor corresponding to a position of a tricep, etc., of the human body in the wearable device may collect an attitude signal of the position of the user's tricep, etc. As another example, when the user performs a dumbbell flying action, the attitude sensor disposed at a position of a deltoid muscle, etc., of the human body may collect an attitude signal of the position of the user's deltoid muscle. In some embodiments, there may be a plurality of attitude sensors in the acquisition module 210. The plurality of attitude sensors may obtain attitude signals of a plurality of parts during the motion of the user. The attitude signals of the plurality of parts may reflect a relative motion between different parts of the human body. For example, an attitude signal at an arm and an attitude signal at a torso may reflect the motion of the arm relative to the torso. In some embodiments, the attitude signal may be associated with the type of the attitude sensor. For example, when the attitude sensor is an angular velocity triaxial sensor, the obtained attitude signal may be angular velocity information. As another example, when the attitude sensor is an angular velocity triaxial sensor and an acceleration triaxial sensor, the obtained attitude signal may be angular velocity information and acceleration information. As another example, when the attitude sensor is a strain gauge sensor, the strain gauge sensor may be disposed at the joint position of the user. By measuring a magnitude of the resistance in the strain gauge sensor that changes with the stretch length, the obtained attitude signal may be displacement information, a stress, etc. A bending angle and a bending direction of the user's joint may be characterized through the attitude signals. It should be noted that parameter information that is configured to reflect the relative motion of the user's body may be the feature information corresponding to the attitude signal. The attitude sensors of different types may be used for obtaining the type of feature information.

In some embodiments, the action signal may include an EMG signal of a specific part of the user's body and an attitude signal of the specific part. The EMG signal and the attitude signal may reflect the motion state of the specific part of the user's body from different angles. In other words, the attitude signal of the specific part of the user's body may reflect an action type, an action amplitude, an action frequency, etc. of the specific part. The EMG signal may reflect the muscle state of the specific part during the motion. In some embodiments, the EMG signal and/or the posture signal of a same body part may better assess whether the action of the part is normative.

In 520, the action of the motion of the user may be monitored at least based on feature information corresponding to the EMG signal or feature information corresponding to the attitude signal.

In some embodiments, the operation may be performed by the processing module 220 and/or the processing device 110. In some embodiments, the feature information corresponding to the EMG signal may include but be not limited to frequency information, amplitude information, or the like, or any combination thereof. The feature information corresponding to the attitude signal may refer to parameter information configured to characterize the relative motion of the user's body. In some embodiments, the feature information corresponding to the attitude signal may include but be not limited to an angular velocity direction, an angular velocity value, an acceleration of the angular velocity, or the like, or any combination thereof. In some embodiments, the feature information corresponding to the attitude signal may also include an angle, displacement information (e.g., a stretched length in a strain gauge sensor), a stress, etc. For example, when the attitude sensor is a strain gauge sensor, the strain gauge sensor may be disposed at the joint position of the user. By measuring a magnitude of the resistance in the strain gauge sensor that changes with the stretch length, the obtained attitude signal may be displacement information, a stress, etc. A bending angle and a bending direction of the user's joint may be characterized through the attitude signals. In some embodiments, the processing module 220 and/or the processing device 110 may extract the feature information (e.g., frequency information, amplitude information) corresponding to the EMG signal or the feature information (e.g., an angular velocity direction, an angular velocity value, an acceleration value of the angular velocity, an angle, displacement information, a stress, etc.) corresponding to the attitude signal, and monitor the action of the motion of the user based on the feature information corresponding to the EMG signal or the feature information corresponding to the attitude signal. The monitoring the action of the motion of the user may include monitoring information related to the user's action. In some embodiments, the action-related information may include an action type, an action count, and an action quality (e.g., whether the user action meets a standard), an action time, or the like, or any combination thereof. The action type may refer to a fitness action taken by the user during the motion. In some embodiments, the action type may include but be not limited to seated chest clamping, squatting, deadlifting, planking, running, swimming, or the like, or any combination thereof. The action count may refer to a count of time(s) that the user performs an action during the motion. For example, the user may perform 10 times of seated chest clamping during the motion, and 10 may be the action times. The action quality may refer to a standard degree of the fitness action performed by the user with respect to a standard fitness action. For example, when the user squats, the processing device 110 may determine the action type of the user's action based on the feature information corresponding to the action signal (e.g., an EMG signal and an attitude signal) of a specific muscle position (e.g., a gluteus maximus, a quadricep, etc.), and determine the quality of the user's squat action based on an action signal of a standard squat action. The action time may refer to the time corresponding to one or more action types of the user or the total time of the motion process.

In some embodiments, the motion monitoring system 100 may also perform smooth processing on the EMG signal to process the EMG signal as a smooth data curve, so as to display the EMG signal to the user for viewing, so that the user may monitor the motion process. In some embodiments, when the action signal of the user is obtained, other physiological parameter information (e.g., a heart rate signal) of the user, and an external condition such as the relative movement or extrusion between the acquisition module 210 and the human body during the motion may affect the quality of the action signal, for example, causing an abnormal signal in the EMG signal, such as an abrupt signal, a missing signal, a saturation signal, an oscillation signal caused by a high-pass filter, etc., and affecting the monitoring of the user action. For convenience of descriptions, the abrupt signal of the EMG signal may be described by a singular point. Exemplary singular points may include a glitch signal, a discontinuous signal, or the like. In some embodiments, during the motion, the vibration caused by the user's heartbeat may cause the abrupt signal in the EMG signal for a short time. In some embodiments, the user may adjust a position of the wearable device 130 during the motion, for example, pulling clothes, pulling a sleeve, etc., which may cause the abrupt signal in the EMG signal for a short time. In some embodiments, the wearable device 130 may be not properly worn, for example, the clothes may be not fit well, and some EMG sensors may have poor contact for a short time or a long time, which may cause the EMG signal to have the abrupt signal for the short time or for the long time. In some embodiments, there may be a motion artifact during the motion of the user. The motion artifact may refer to signal noise generated by a movement of a muscle relative to an EMG module during the motion of the user in the process of obtaining the EMG signal. The motion artifact may lead to the abrupt signal in the EMG signal for a short time or for a long time. In some embodiments, the wearable device 130 may be not properly worn, for example, the clothes may be not fit well, and some EMG sensors may have poor contact for a short time or a long time, which may also cause missing of the EMG signal or saturation of the EMG signal. When a positive electrode and a negative electrode of the EMG sensor are in poor contact, the positive electrode and the negative electrode may not collect a correct EMG signal. At this time, there may be a phenomenon of signal missing in the EMG signal, that is, there may be a missing signal in the EMG signal. When a part of the positive electrode and the negative electrode in the EMG sensor is in poor contact, the part of the positive electrode and the negative electrode may collect the EMG signal, and another part of the positive electrode and the negative electrode may collect a power frequency signal. Since an amplitude of the power frequency signal is much higher than that of the EMG signal, at this time, there may be a saturation signal in the EMG signal, that is, a phenomenon that the signal amplitude is too high to reach a saturated state may occur. In some embodiments, the motion monitoring system 100 may perform a direct current (DC) removing on the EMG signal by using a high-pass filter, which may cause an oscillating signal in the EMG signal after the DC removing.

In order to improve the user experience, the motion monitoring system 100 may also provide a motion data processing method to identify an abnormal signal in the EMG signal and correct the identified abnormal signal to make the corrected abnormal signal conform to the action signal during an actual motion of the user, thereby improving the user experience. The motion data processing method and the motion monitoring system may also remind the user that the device is worn abnormally in time when the abnormal signal is identified, thereby making data collection more accurate. The motion data processing method may be executed on the processing device 110, or on the wearable device 130. Specifically, the motion data processing method may be executed by the processing module 220 on the wearable device 130, or on the mobile terminal device 140. For convenience of presentation, the following descriptions may be illustrated by taking the motion data processing method executed on the processing module 220 in the wearable device 130 as an example. At this time, the action signal collected by the acquisition module of the wearable device 130 may be directly transmitted to the processing module 220 for data processing, and may not need to be transmitted to the processing device 110 or the mobile terminal device 140 via the network, thereby reducing the time for data transmission, improving the efficiency of motion data processing, and further improving the real-time performance of motion data processing.

Figure 6:
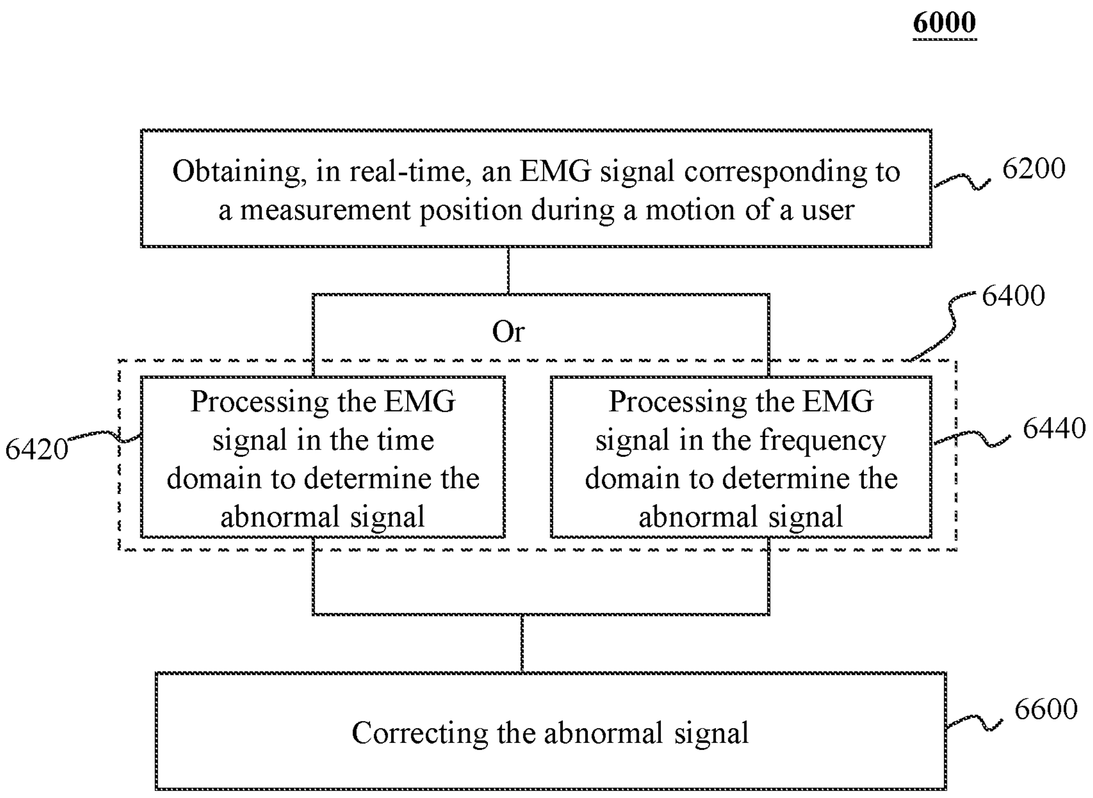
FIG. 6 is a flowchart illustrating an exemplary process for processing motion data according to some embodiments of the present disclosure.

FIG. 6 is a flowchart illustrating an exemplary process 6000 for processing motion data according to some embodiments of the present disclosure. As shown in FIG. 6, the process 6000 may include following operations.

In 6200, an electromyography (EMG) signal corresponding to a measurement position during a motion of a user may be obtained in real-time.

The EMG signal may be collected by the acquisition module 210. In some embodiments, an EMG sensor in the acquisition module 210 may collect the EMG signal during the motion of the user. For example, when the user clamps the chest in a sitting position, the EMG sensor corresponding to a position of a pectoral muscle, a latissimus dorsum, etc., of the human body in the wearable device may collect an EMG signal corresponding to a muscle position of the user. As another example, when the user squats, the EMG sensor corresponding to a position of a gluteus maximus, a quadricep, etc., of the human body in the wearable device may collect an EMG signal corresponding to a muscle position of the user. As another example, when the user is running, the EMG sensor corresponding to a position of a gastrocnemius, etc., of the human body in the wearable device may collect an EMG signal of the position of the gastrocnemius, etc. of the human body. The EMG signal may reflect a muscle state of a specific part during the motion of the user. The real-time may be that the processing module 220 periodically obtains the EMG signal from the acquisition module 220 in a short time period.

In some embodiments, the EMG signal may be a signal directly collected by the EMG sensor in the acquisition module 210. In some embodiments, the EMG signal may also be a signal obtained by performing a DC removing algorithm on the signal directly collected by the EMG sensor. The DC removing algorithm may remove a DC component in the EMG signal by calculation. The DC removing algorithm may include a de-averaging algorithm, a high-pass filtering algorithm, or the like, or any combination thereof. In order to ensure the real-time performance of the DC removing algorithm, the de-averaging algorithm may be that de-averaging is performed frame by frame.

When the DC removing is performed on the EMG signal by using the DC removing algorithm, after de-averaging is performed on an abnormal signal, a new abnormal signal may appear at the abnormal signal. When the DC removing is performed on the EMG signal by using the high-pass filter, an oscillation signal may appear at a transition of an actual signal. In addition, the usage of the high-pass filter may cause a phenomenon that the EMG signal has a convergence delay in an early stage. The oscillation signal is also an abnormal signal, which may also affect the monitoring of the motion of the user.

Through researches of the high-pass filter, it is found that the smaller a cutoff frequency used by the high-pass filter is, the slower a convergence speed and the longer the time of convergence takes in the early stage, resulting in a longer signal convergence delay and a worse real-time performance. Conversely, the larger the cutoff frequency used by the high-pass filter is, the faster the convergence speed and the shorter the time of convergence takes in the early stage, resulting in a shorter signal convergence delay and a better real-time performance. At the same time, the lower the cutoff frequency used by the high-pass filter, the lower an oscillation height of the oscillation signal caused by the high-pass filter may be and the shorter a duration of the oscillation signal may be. Conversely, the higher the cutoff frequency used by the high-pass filter, the higher the oscillation height of the oscillation signal caused by the high-pass filter may be, and the longer the duration of the oscillation signal may be. In order to ensure the real-time performance of the EMG signal, the processing module 220 may predetermine a preset range of the convergence delay based on the real-time performance, and determine a target range of the cutoff frequency based on the relationship between the cutoff frequency, the convergence speed and the convergence delay.

In 6400, the abnormal signal in the EMG signal may be determined based on the EMG signal.

In some embodiments, operation 6400 may include preprocessing the EMG signal in a frequency domain or in a time domain. Feature information corresponding to the EMG signal may be obtained based on the pre-processed EMG signal, thus the abnormal signal in the EMG signal may be determined, and an action of the motion of the user may be monitored. Specifically, operation 6400 may include the following operations.

In 6420, the EMG signal may be processed in the time domain to determine the abnormal signal; or in 6440, the EMG signal may be processed in the frequency domain to determine the abnormal signal.

Figure 7:
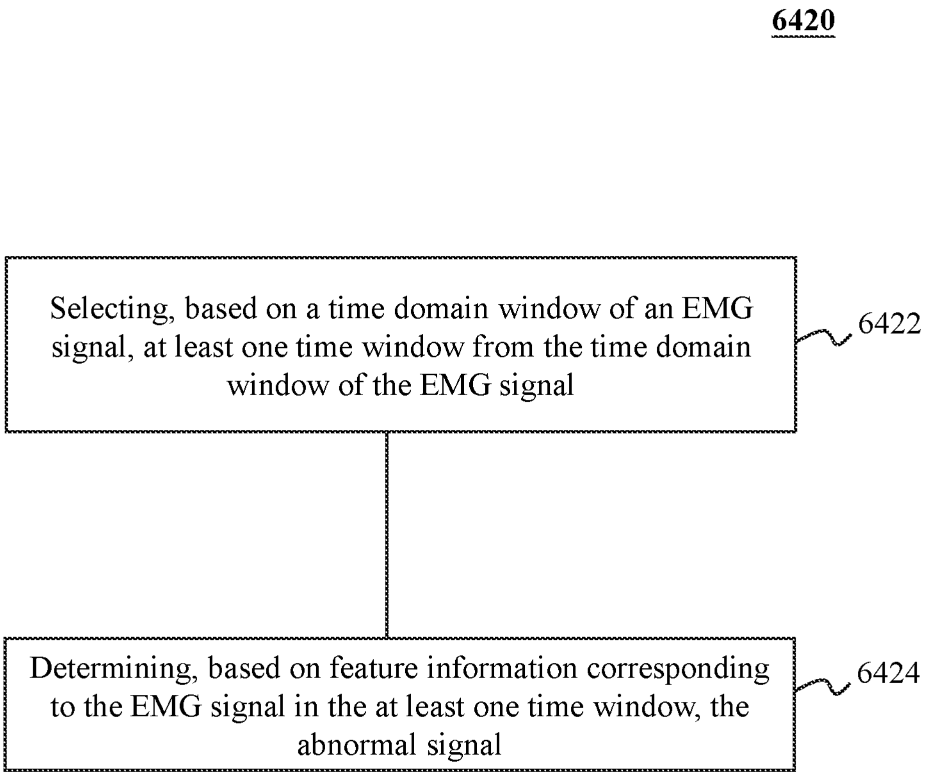
FIG. 7 is a flowchart illustrating an exemplary process for processing an electromyography (EMG) signal in a time domain according to some embodiments of the present disclosure.

FIG. 7 is a flowchart illustrating an exemplary process for processing an EMG signal in a time domain according to some embodiments of the present disclosure. Operation 6420 is shown in FIG. 7. As shown in FIG. 7, operation 6420 may include the following operations.

In 6422, based on a time domain window of an EMG signal, at least one time window from the time domain window of the EMG signal may be determined.

Each of the at least one time window may cover a different time range. In some embodiments, the time domain window may include at least one specific window. A specific window may refer to a window with a specific time length selected in the time domain window. For example, when a time length of the time domain window of the EMG signal is 3 seconds, the time length of the specific window may be 100 milliseconds. In some embodiments, the specific window may include at least one different time window. In some embodiments, the specific window may include a time window. In some embodiments, the specific window may include a plurality of time windows. When the specific window includes a plurality of time windows, merely by way of example, the specific window may include a first time window and a second time window. The first time window may refer to a window corresponding to a partial time length of the specific window. For example, when the time length of the specific window is 100 milliseconds, a time length of the first time window may be 80 milliseconds. The second time window may refer to another window with a partial time length of a specific window. For example, when the specific window is 100 milliseconds, the second time window may be 20 milliseconds. In some embodiments, the first time window and the second time window may be consecutive time windows in one same specific window. In some embodiments, the first time window and the second window may also be two inconsecutive or overlapping time windows in one same specific window. In some embodiments, the processing module 220 may, based on the time domain window of the EMG signal, slide and update the specific window sequentially from a time starting point of the time domain window of the EMG signal based on a specific time length, and may further divide the updated specific window into the first window and the second window. The specific time length mentioned herein may be less than 1 second, 2 seconds, 3 seconds, etc. For example, the processing module 220 may select a specific window with a specific time length of 100 milliseconds, and divide the specific window into a first time window of 80 milliseconds and a second time window of 20 milliseconds. Further, the specific window may be updated by sliding in a time direction. A sliding distance may be a time length (e.g., 20 milliseconds) of the second window, or may be another appropriate time length, such as 30 milliseconds, 40 milliseconds, etc. As mentioned, each of different time windows may cover a different time range. For convenience of descriptions, a time range covered by the first time window may be defined as a previous time window, and a time range covered by the second time window may be defined as a subsequent time window. That is, the time range corresponding to the first time window may be previous to the time range corresponding to the second time window.

In some embodiments, the time length corresponding to the first time window may be greater than the time length corresponding to the second time window. In some embodiments, the specific time length corresponding to the specific window may be less than 1 second. In some embodiments, a ratio of the time length corresponding to the first time window to the time length corresponding to the second time window may be greater than 2. In some embodiments, the selection of the time length corresponding to the first time window, the time length corresponding to the second time window, and the specific time length corresponding to the specific window may ensure that a length of a shortest glitch signal (e.g., 40 milliseconds) may be removed and a high signal-to-noise ratio may be ensured. On the other hand, a calculation amount of the system may be relatively small, the repeated calculation of the system may be reduced, and the time complexity may be reduced, thus the computing efficiency and calculation accuracy of the system may be improved.

When the specific window includes a time window, the specific window may include a first time window or a second time window. Merely by way of example, when the specific window includes a time window, the specific window may include the second time window.

In 6424, the abnormal signal may be determined based on feature information corresponding to the EMG signal in the at least one time window.

In some embodiments, the feature information may include amplitude information or statistical information of the amplitude information, or any combination thereof. In some embodiments, the amplitude information may be an average amplitude or a square of the average amplitude of the EMG signal corresponding to each time window in the at least one time window. In some embodiments, the statistical information of the amplitude information may include an entropy, a variance, a standard deviation, a standard deviation of the standard deviation, a zero-crossing rate of the amplitude information, or any combination thereof. The entropy may be regarded as a measure of disorder in a system. The variance, the standard deviation, and the standard deviation of the standard deviation may be configured to evaluate a degree of data dispersion. The zero-crossing rate may refer to a ratio of a sign change, such as a signal changing from positive to negative or reverse.

In some embodiments, a normal EMG signal may generally be a short-term stable signal, that is, an average value and a variance of an amplitude of the EMG signal in a certain time period may be stable and have a small fluctuation. The abnormal signal such as an abrupt signal, a missing signal, a saturation signal, etc. may be a unstable signal. Therefore, amplitude information of the normal EMG signal and statistical information of the amplitude information may be obviously different from amplitude information of the abnormal signal and statistical information of the amplitude information. The motion data processing method 6000 may include identifying the abnormal signal based on feature information corresponding to the EMG signal. In some embodiments, the processing module 220 may obtain amplitude information or statistical information of the amplitude information corresponding to the EMG signal in different time windows (e.g., a first time window and/or a second time window) to determine a position of the abnormal signal. The detailed descriptions regarding the determination of the position of the abnormal signal based on the feature information corresponding to the EMG signal in different time windows may be illustrated as follows.

For convenience of descriptions, the following descriptions may be illustrated by taking that the feature information is amplitude information as an example. Those skilled in the art should understand that the amplitude information including statistical information of the amplitude information is also within the scope of the present disclosure. When the feature information includes the statistical information of the amplitude information, an identification method thereof may be same as an identification method in which the feature information is the amplitude information, which may be not repeated in the present disclosure.

Figure 8:
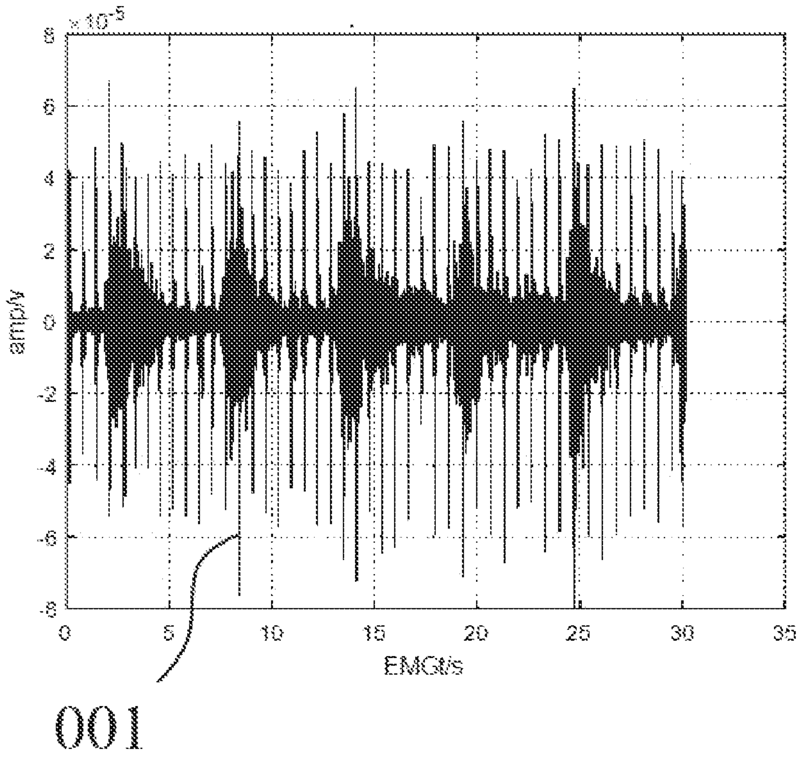
FIG. 8 is a schematic diagram illustrating an exemplary abrupt signal according to some embodiments of the present disclosure.

As mentioned, in some embodiments, an abnormal signal may include an abrupt signal. FIG. 8 is a schematic diagram illustrating an exemplary abrupt signal according to some embodiments of the present disclosure. As shown in FIG. 8, 001 is an abrupt signal. As mentioned, the abrupt signal of the EMG signal 001 may be described by a singular point. Exemplary singular points may include a glitch signal, a discontinuous signal, or the like. For convenience of descriptions, the following descriptions may be illustrated by taking that the singular point is a glitch signal as an example. The singular point may refer to discontinuity of a signal caused by an abrupt change of an amplitude of the EMG signal at a certain time point. As another example, the EMG signal may be relatively smooth in shape, and the amplitude of the EMG signal may not change abruptly, but a first-order differential of the EMG signal may change abruptly, and the first-order differential may be discontinuous.

When the abrupt signal is identified, the descriptions may be illustrated by taking that at least one time window includes a plurality of time windows as an example. For convenience of descriptions, the descriptions may be illustrated by taking that the plurality of windows are a first time window and a second time window, and the feature information is amplitude information as an example. Those skilled in the art should understand that the plurality of time windows include more than two time windows, which may also be within the scope of the present disclosure.

Figure 9:
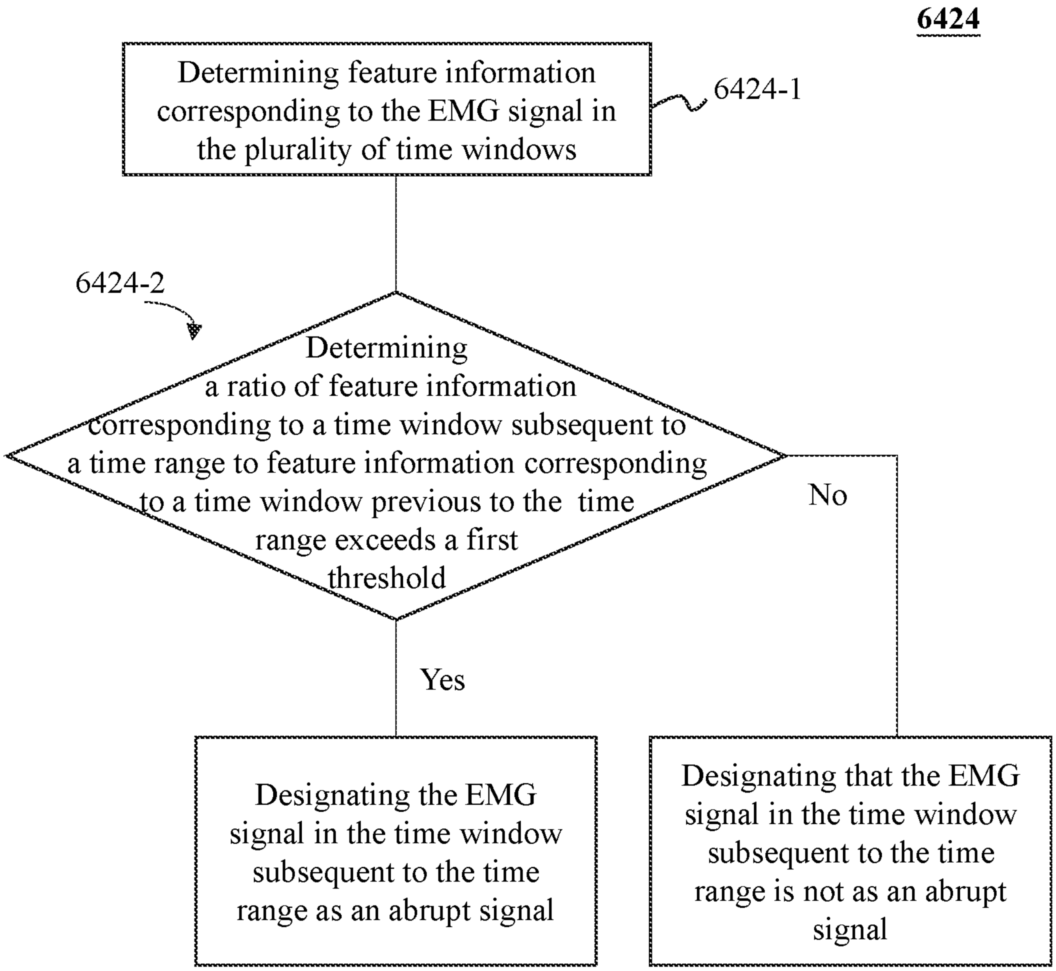
FIG. 9 is a flowchart illustrating an exemplary process for identifying an abrupt signal according to some embodiments of the present disclosure.

FIG. 9 is a flowchart illustrating an exemplary process for identifying an abrupt signal according to some embodiments of the present disclosure. Operation 6424 is shown in FIG. 9. As shown in FIG. 9, operation 6424 may include the following operations.

In 6424-1, feature information corresponding to the EMG signal in the plurality of time windows may be determined.

In 6424-1, feature information corresponding to the EMG signal in each time window of the plurality of time windows may be determined. The plurality of time windows may correspond to a plurality pieces of feature information, and the plurality of time windows may correspond to the plurality pieces of feature information one by one. The descriptions may be illustrated by taking that the plurality of time windows include a first time and a second time window and the feature information is amplitude information as an example. In 6424-1, first amplitude information corresponding to the EMG signal in the first window and second amplitude information corresponding to the EMG signal in the second window may be determined. In some embodiments, the processing module 220 may select a time length of the first time window and a time length of the second time window, and extract first amplitude information corresponding to the EMG signal in the time length of the first time window time and second amplitude information corresponding to the EMG signal in the time length of the second time window. In some embodiments, the first amplitude information may include an average amplitude of the EMG signal in the first time window or a square of the average amplitude of the EMG signal in the first time window. The second amplitude information may include an average amplitude of the EMG signal in the second time window or a square of the average amplitude of the EMG signal in the second time window. For example, the processing module 220 may select the time length of the first time window as 80 milliseconds and extract the first amplitude information corresponding to the EMG signal in the first time window. The processing module 220 may select the time length of the second time window as 20 milliseconds and extract the second amplitude information corresponding to the EMG signal in the second time window.

In some embodiments, the selection of the time length of the first time window and the time length of the second time window may be related to a length of a shortest glitch signal and a calculation amount of the system. In some embodiments, the time length of the first time window and the time length of the second time window may be selected based on a feature of a glitch signal. A time length of an ECG glitch signal may be 40 milliseconds –100 milliseconds. A time interval between two glitch signals in the ECG signal may be about 1 s. Two sides of a peak point of the glitch signal may be basically symmetrical. An amplitude distribution on two sides of the glitch signal may be relatively average. In some embodiments, when the glitch signal is the ECG signal, a time length smaller than a length of the glitch signal may be selected. For example, half of the length of the glitch signal may be selected as the time length of the second time window. The time length of the first time window may be greater than the length of the second time window, for example, 4 times the time length of the second time window. In some embodiments, the time length of the first time window may only need to be within a range of a glitch signal interval (about 1 s) minus the time length of the second time window. It should also be noted that the time length of the first time window and the time length of the second time window may be not limited to the above descriptions. As long as a sum of the time length of the second time window and the time length of the first time window is smaller than the time interval between two adjacent glitch signals, the time length of the second time window is smaller than the length of a single glitch signal, or the amplitude of the EMG signal in the second time window and the amplitude of the EMG signal in the first time window may be distinct efficiently.

In 6424-2, a ratio of feature information corresponding to a time window subsequent to a time range to feature information corresponding to a time window previous to the time range may be determined to exceed a predetermined first threshold, and the EMG signal in the time window subsequent to the time range may be designated as the abrupt signal.

As mentioned, the time range corresponding to the first time window may be the previous to the time range corresponding to the second time window. That is, the time window previous to the time range may be the first time window. The time window subsequent to the time range may be the second time window. The determining a ratio of feature information corresponding to a time window subsequent to the time range to feature information corresponding to a time window previous to the time range may include determining a ratio of feature information corresponding to the EMG signal in the second time window to feature information corresponding to the EMG signal in the first time window, that is, a ratio of the second amplitude information corresponding to the EMG signal in the second time window and the first amplitude information corresponding to the EMG signal in the first time window.

In some embodiments, the processing module 220 may determine whether the ratio of the second amplitude information corresponding to the EMG signal in the second time window to the first amplitude information corresponding to the EMG signal in the first time window exceeds the first threshold. The first threshold may be stored in a storage or a disk of the wearable device 130, or may also be stored in the processing device 110, or adjusted based on an actual situation. In some embodiments, the processing module 220 may perform signal correction processing on the EMG signal in the second time window based on a determination result of a relationship between the ratio of the second amplitude information to the first amplitude information and the first threshold in operation 6424-2. In some embodiments, if the processing module 220 determines that the ratio of the second amplitude information to the first amplitude information exceeds the first threshold, operation 6424-2 may include determining that the EMG signal in the second time window is the abrupt signal, and process the EMG signal in the second time window through operation 6600 to correct the abrupt signal. In some embodiments, the processing the EMG signal in the second time window may include performing signal correction processing on the EMG signal in the second time window based on the EMG signal within a specific time range previous or subsequent to the second time window. More detailed descriptions for operation 6600 may be described in the following descriptions.

In other embodiments, if the ratio of the second amplitude information to the first amplitude information is determined to be smaller than or equal to the first threshold by the processing module 220, the processing module 220 may retain the EMG signal in the second time window. In some embodiments, the processing module 220 may execute to retain the EMG signal in the second window based on the determination result of the relationship between the ratio of the second amplitude information to the first amplitude information and the first threshold. For example, in some embodiments, the ratio of the second amplitude information to the first amplitude information may be smaller than or equal to the first threshold value, then the EMG signal in the second window corresponding to the second amplitude information may be not the abrupt signal, and the EMG signal may be retained, that is, the EMG signal in the second window may be retained.

It should be noted that during the process of muscle exertion of the user, charge may gradually accumulate, and the amplitude of the EMG signal may gradually increase, so in the absence of a glitch signal, the amplitude of the EMG signal in two adjacent time windows (e.g., the first time window and the second time window) may not abruptly change. In some embodiments, the glitch signal may be processed in real-time by determining and removing the glitch signal in the EMG signal based on operation 6424, so that the wearable device 130 or the mobile terminal device 140 may feed back a motion state to the user in real-time, thereby helping the user to exercise more scientifically.

In some embodiments, a way of determining the singular point in the EMG signal may also include, but be not limited to a Fourier transformation, a wavelet transformation, a fractal dimension, or the like, or any combination thereof, which may be not repeated in the present disclosure.

Figure 10:
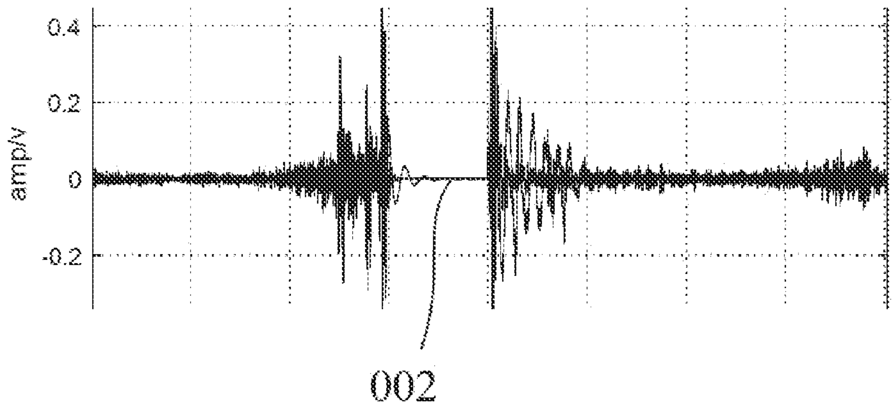
FIG. 10 is a schematic diagram illustrating an exemplary missing signal according to some embodiments of the present disclosure.

As mentioned, in some embodiments, an abnormal signal may include a missing signal. FIG. 10 is a schematic diagram illustrating an exemplary missing signal according to some embodiments of the present disclosure. As shown in FIG. 10, 002 is a missing signal. As mentioned, the missing signal of the EMG signal may be formed by loss of a signal caused by complete detachment of a positive electrode and a negative electrode of an EMG sensor. An amplitude of the missing signal may be basically 0 or close to 0.

When the missing signal is identified, the descriptions may be illustrated by taking that at least one time window includes one time window as an example. For convenience of descriptions, the descriptions may be illustrated by taking that the at least one time window is a second time window and the feature information is amplitude information as an example. Those skilled in the art should understand that the at least one time window may include more than one time window, which is also within the scope of the present disclosure.

Figure 11:
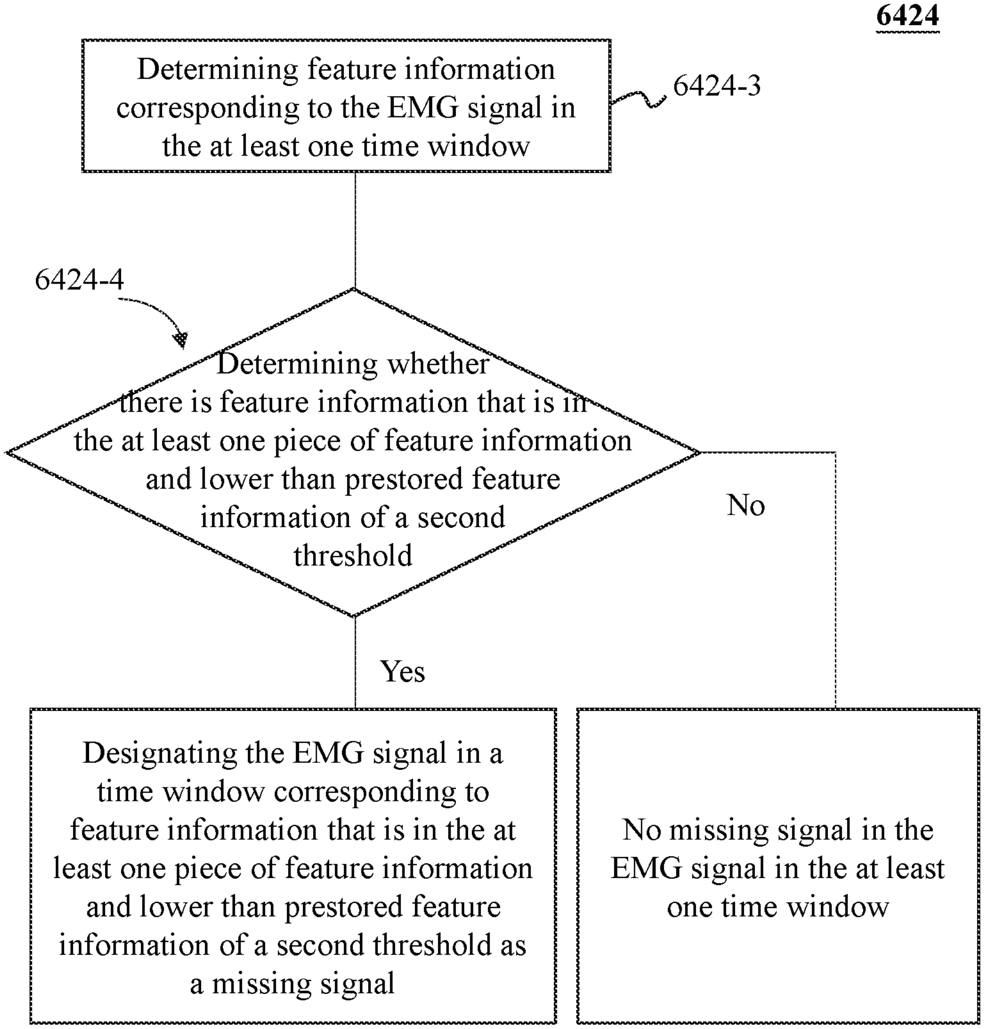
FIG. 11 is a flowchart illustrating an exemplary process for identifying a missing signal according to some embodiments of the present disclosure.

FIG. 11 is a flowchart illustrating an exemplary process for identifying a missing signal according to some embodiments of the present disclosure. As shown in FIG. 11, operation 6424 may include the following operations.

In 6424-3, feature information corresponding to the EMG signal in the at least one time window may be determined.

In 6424-3, feature information corresponding to the EMG signal in each time window of the at least one time window may be determined. The at least one time window may correspond to at least one piece of feature information, and the at least one time window may correspond to the at least one piece of feature information one by one. The descriptions may be illustrated by taking that at least one time window includes a second time window and the feature information is amplitude information as an example. The operation may be basically the same as the operation 6424-1, which may be not repeated herein.

In some embodiments, the selection of a time length of the second time window may be related to a length of a shortest missing signal and a calculation amount of the system. In some embodiments, the time length of the second time window may be selected based on the effect of the missing signal on data sampling of a smooth curve. For example, the length of the second time window may be smaller than a length of a time period of data sampling. For example, half of the length of the time period of the data sampling may be the length of the second time window. It should also be noted that the selection of the time length of the second time window is not limited to the above descriptions, as long as the length of the time period of the second time window is smaller than the length of the time period of the data sampling. More detailed descriptions of the data sampling may be described in the following descriptions.

In 6424-4, the EMG signal in a time window corresponding to feature information that is in the at least one piece of feature information and lower than prestored feature information of a second threshold may be designated as a missing signal.

As mentioned, the amplitude of the missing signal may be basically 0 or close to 0. Therefore, amplitude information of the missing signal may be generally lower than the second threshold. The second threshold herein may be stored in a storage or a disk of the wearable device 130, or may also be stored in the processing device 110, or adjusted based on an actual situation. The second threshold may be calculated and stored in advance before operation 6424-4. In some embodiments, the second threshold may be background noise of the system. The background noise of the system may be calculated based on a static EMG signal collected when the user is at rest or when the wearable device 130 is not in usage. In some embodiments, the second threshold may also be a minimum statistical value based on a historical EMG signal, for example, a minimum value of a normal EMG signal collected by the EMG sensor in a historical time point. Specifically, operation 6424-4 may include determining a relationship between the feature information corresponding to the EMG signal in the at least one piece of feature information (e.g., the second time window) and the second threshold. In some embodiments, if the processing module 220 determines that the second amplitude information is smaller than the second threshold, then operation 6424-4 may include determining that the EMG signal in the second time window is the missing signal, and process the EMG signal in the second time window through operation 6600 to correct the missing signal. In some embodiments, the processing the EMG signal in the second time window may include performing signal correction processing on the EMG signal in the second time window based on the EMG signal within a specific time range previous or subsequent to the second time window. More detailed description of operation 6600 may be described in the following descriptions.

In other embodiments, if the processing module 220 determines that the feature information exceeds the second threshold, there may be no missing signal in the at least one time window. For example, if the processing module 220 determines that the second amplitude information exceeds or is equal to the second threshold, the processing module 220 may retain the EMG signal in the second window. In some embodiments, the processing module 220 may execute to retain the EMG signal in the second window based on a determination result of the relationship between the second amplitude information and the second threshold. For example, in some embodiments, if the second amplitude information exceeds or is equal to the second threshold, the EMG signal in the second time window corresponding to the second amplitude information may be not the missing signal, and the EMG signal may be retained, that is, the EMG signal in the second time window may be retained.

Figure 12:
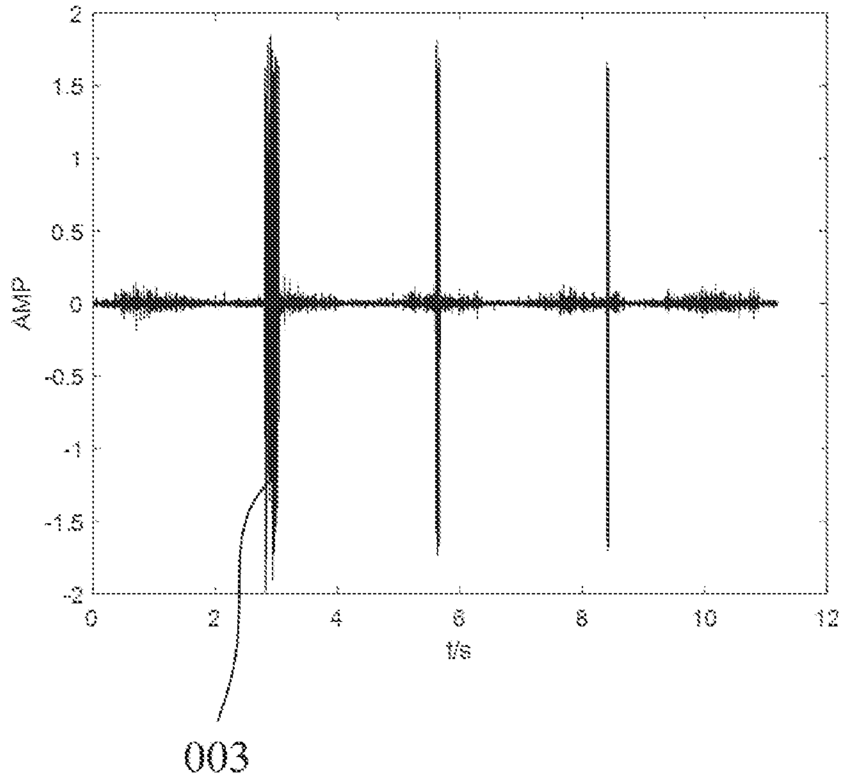
FIG. 12 is a schematic diagram illustrating an exemplary saturation signal according to some embodiments of the present disclosure.

As mentioned, in some embodiments, an abnormal signal may include a saturation signal. FIG. 12 is a schematic diagram illustrating an exemplary saturation signal according to some embodiments of the present disclosure. As shown in FIG. 12, 003 is a saturation signal. As mentioned, the saturation signal of the EMG signal may be formed by signal saturation caused by partial detachment of a positive electrode and a negative electrode of an EMG sensor. An amplitude of the saturation signal may be much higher than that of the normal EMG signal.

When the saturation signal is identified, the descriptions may be illustrated by taking the at least one time window including one time window as an example. For convenience of descriptions, the description may be illustrated by taking the at least one time window being the second time window and the feature information being amplitude information as an example. Those skilled in the art should understand that the at least one time window may include more than one time window, which is also within the scope of the present disclosure.

Figure 13:
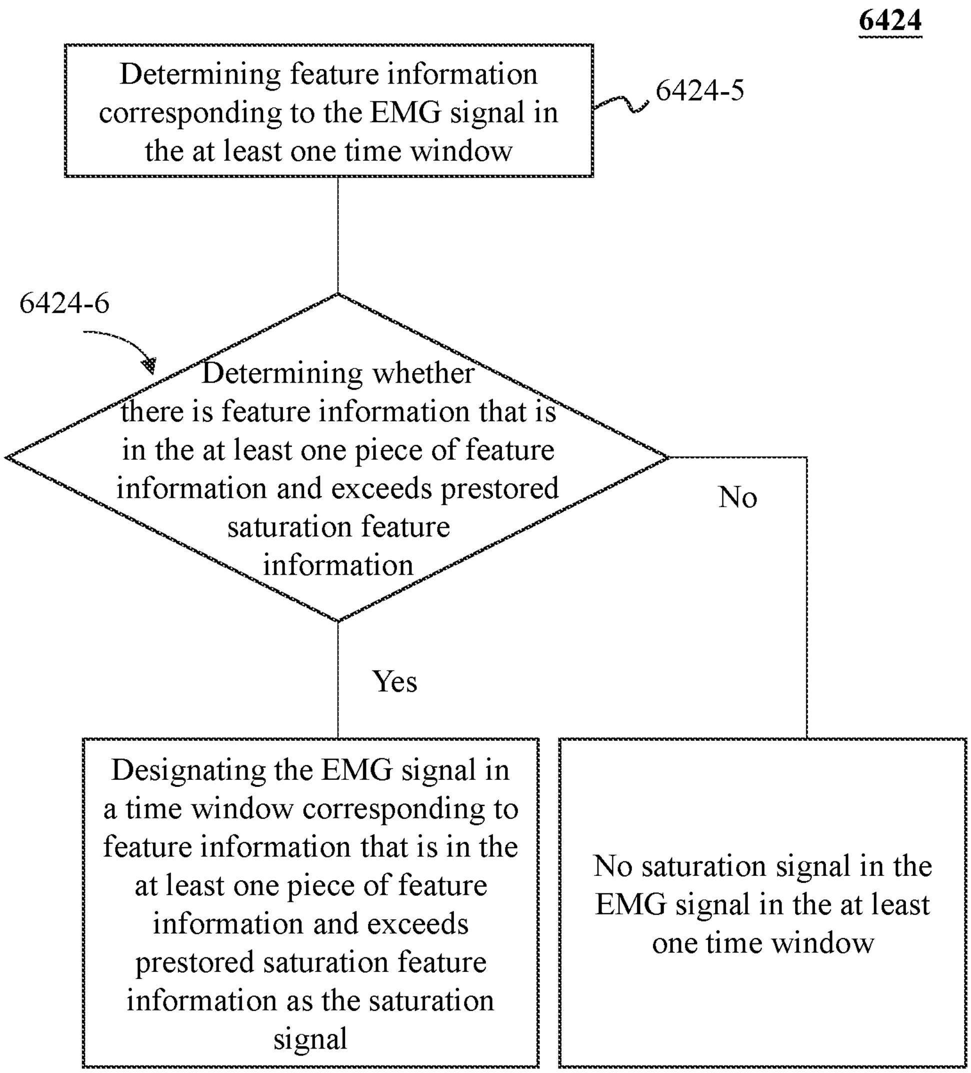
FIG. 13 is a flowchart illustrating an exemplary process for identifying a saturation signal according to some embodiments of the present disclosure.

FIG. 13 is a flowchart illustrating an exemplary process for identifying a saturation signal according to some embodiments of the present disclosure. As shown in FIG. 13, operation 6424 may include the following operations.

In 6424-5, feature information corresponding to the EMG signal in the at least one time window may be determined.

In 6424-5, feature information corresponding to the EMG signal in each time window of the at least one time window may be determined. The at least one time window may correspond to at least one piece of feature information, and the at least one time window may correspond to the at least one piece of feature information one by one. The descriptions may be illustrated by taking that the at least one time window includes the second time window and the feature information is the amplitude information as an example. The operation may be basically the same as operation 6424-1, which may be not repeated herein.

In some embodiments, the selection of the time length of the second time window may be related to a length of a shortest saturation signal and a calculation amount of the system. In some embodiments, the time length of the second time window may be selected based on the effect of the saturation signal on data sampling of a smooth curve. For example, the length of the second time window may be smaller than a length of a time period of data sampling. For example, half of the length of the time period of the data sampling may be the length of the second time window. It should also be noted that the selection of the time length of the second time window is not limited to the above descriptions, as long as the length of the time period of the second time window is smaller than the length of the time period of the data sampling. More detailed description of the data sampling may be described in the following descriptions.

In 6424-6, the EMG signal in a time window corresponding to feature information that is in the at least one piece of feature information and exceeds prestored saturation feature information may be designated as the saturation signal.

As mentioned, the amplitude of the saturation signal may be much higher than that of the normal EMG signal. In some embodiments, the processing module 220 may determine whether the feature information exceeds the saturation feature information. The saturation feature information herein may be stored in a storage or a disk of the wearable device 130, or may also be stored in the processing device 110, or adjusted based on an actual situation. The saturation feature information may be determined and stored in advance before operation 6424-6. The saturation feature information may be determined based on a saturation EMG signal collected when the positive electrode and the negative electrode of the EMG sensor are partially detached. Specifically, operation 6424-6 may include determining a relationship between the feature information corresponding to the EMG signal in the at least one piece of feature information (e.g., the second time window) and the saturation feature information. In some embodiments, if the processing module 220 determines that the second amplitude information exceeds the saturation feature information, operation 6424-6 may include determining that the EMG signal in the second time window is the saturation signal, and processing the EMG signal in the second time window through operation 6600 to correct the saturation signal. In some embodiments, the processing the EMG signal in the second time window may include performing signal correction processing on the EMG signal in the second time window based on the EMG signal within a specific time range previous or subsequent to the second time window. More detailed description regarding operation 6600 may be described in the following descriptions.

In other embodiments, if the processing module 220 determines that the feature information is less than the saturation feature information, it may be determined that there is no saturation signal in the at least one time window. For example, if the processing module 220 determines that the second amplitude information is less than or equal to the saturation feature information, the processing module 220 may retain the EMG signal in the second window. In some embodiments, the processing module 220 may execute to retain the EMG signal in the second window based on a determination result of the relationship between the second amplitude information and the saturation feature information. For example, in some embodiments, if the second amplitude information is less than or equal to the saturation feature information, the EMG signal in the second time window corresponding to the second amplitude information may be not the saturation signal, and the EMG signal may be retained, that is, the EMG signal in the second window may be retained.

Figure 14:
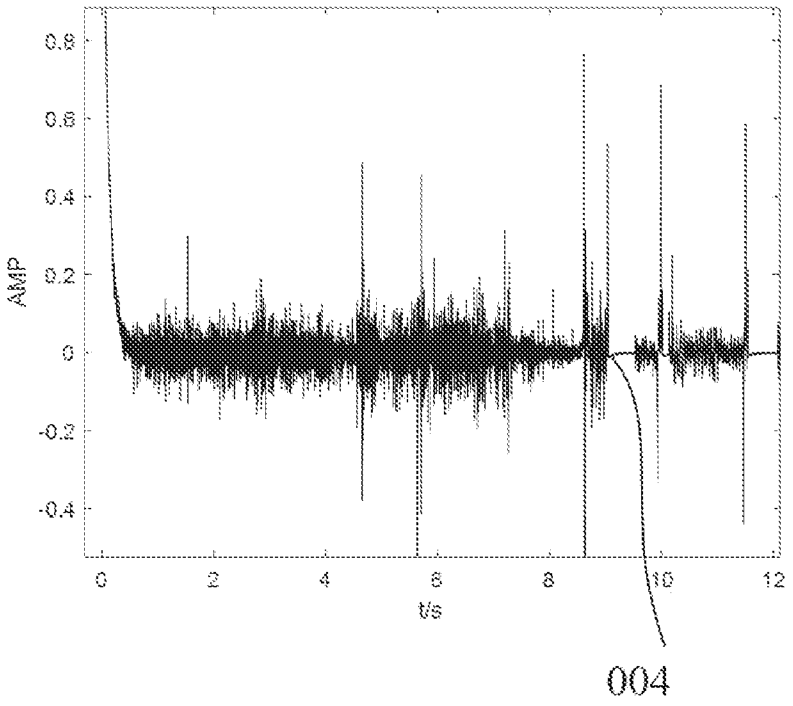
FIG. 14 is a schematic diagram illustrating an exemplary oscillation signal according to some embodiments of the present disclosure.

As mentioned, in some embodiments, an abnormal signal may include an oscillation signal caused by a high-pass filtering algorithm. FIG. 14 is a schematic diagram illustrating an exemplary oscillation signal according to some embodiments of the present disclosure. As shown in FIG. 14, 004 is an oscillation signal.

Figure 15:
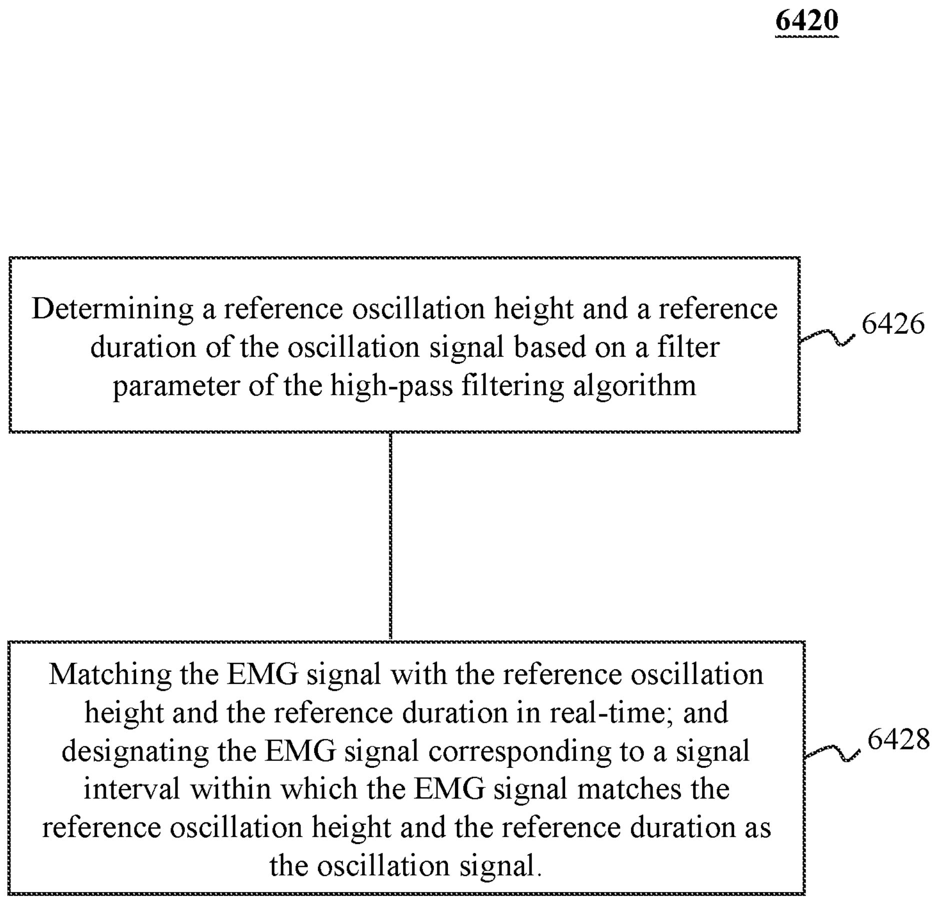
FIG. 15 is a flowchart illustrating an exemplary process for identifying an oscillation signal according to some embodiments of the present disclosure.

FIG. 15 is a flowchart illustrating an exemplary process for identifying an oscillation signal according to some embodiments of the present disclosure. Operation 6420 may be shown in FIG. 15. As shown in FIG. 15, operation 6420 may include the following operations.

In 6426, a reference oscillation height and a reference duration of the oscillation signal may be determined based on a filter parameter of the high-pass filtering algorithm.

As mentioned, the lower the cutoff frequency used by the high-pass filter is, the lower an oscillation height of the oscillation signal caused by the high-pass filter and the shorter a duration of the oscillation signal may be. In contrast, the higher the cutoff frequency used by the high-pass filter, the higher the oscillation height of the oscillation signal caused by the high-pass filter may be, and the longer the duration of the oscillation signal may be. The processing module 220 may determine the reference oscillation height and the reference duration of the oscillation signal based on the cutoff frequency of the high-pass filter. The filter parameter may include the cutoff frequency.

In 6428, the EMG signal may be matched with the reference oscillation height and the reference duration in real-time. The EMG signal corresponding to a signal interval within which the EMG signal matches the reference oscillation height and the reference duration may be designated as the oscillation signal.

The processing module 220 may match the EMG signal with the reference oscillation height and the reference duration corresponding to the EMG signal to search for the oscillation signal from the EMG signal. In some embodiments, if the processing module 220 determines that there is a signal interval in the EMG signal that matches the reference oscillation height and the reference duration, the processing module 220 may determine that the EMG signal corresponding to the matched signal interval is the oscillation signal, and process the oscillation signal based on operation 6600 to correct the oscillation signal. In some embodiments, the processing the oscillation signal may include performing signal correction processing on the oscillation signal based on the EMG signal within a specific time range previous or subsequent to the oscillation signal. More detailed description of operation 6600 may be described in the following descriptions.

In other embodiments, if the processing module 220 determines that there is a signal interval in the EMG signal that does not match the reference oscillation height and the reference duration, the processing module 220 may determine that the EMG signal corresponding to the mismatched signal interval is not the oscillating signal, and the processing module may retain the EMG signal in the mismatched signal interval.

As mentioned, operation 6400 may also include operation 6440. In 6440, the EMG signal in a frequency domain may be processed to determine the abnormal signal. In some embodiments, the processing the EMG signal in the frequency domain may include filtering the EMG signal in the frequency domain to select or retain a component of a specific frequency range in the EMG signal in the frequency domain. In some embodiments, the frequency range of the EMG signal obtained by the acquisition module 210 may be 1 Hz-1000 Hz, which may be filtered and the EMG signal of the specific frequency range (e.g., 30 Hz-150 Hz) may be selected for subsequent processing. In some embodiments, the specific frequency range may be 10 Hz-500 Hz. Preferably, the specific frequency range may be 15 Hz-300 Hz. More preferably, the specific frequency range may be 30 Hz-150 Hz. In some embodiments, the filtering may include a low-pass filter processing. In some embodiments, a low-pass filter may include an inductor-capacitor (LC) passive filter, a resistor-capacitor (RC) passive filter, a RC active filter, and a passive filter composed of a specific component. In some embodiments, the passive filter composed of the special component may include a piezoelectric ceramic filter, a crystal filter, a surface acoustic wave filter, or any combination thereof. It should be noted that the specific frequency range is not limited to the above range, and may also be other ranges, which may be selected based on an actual situation.

Figure 16:
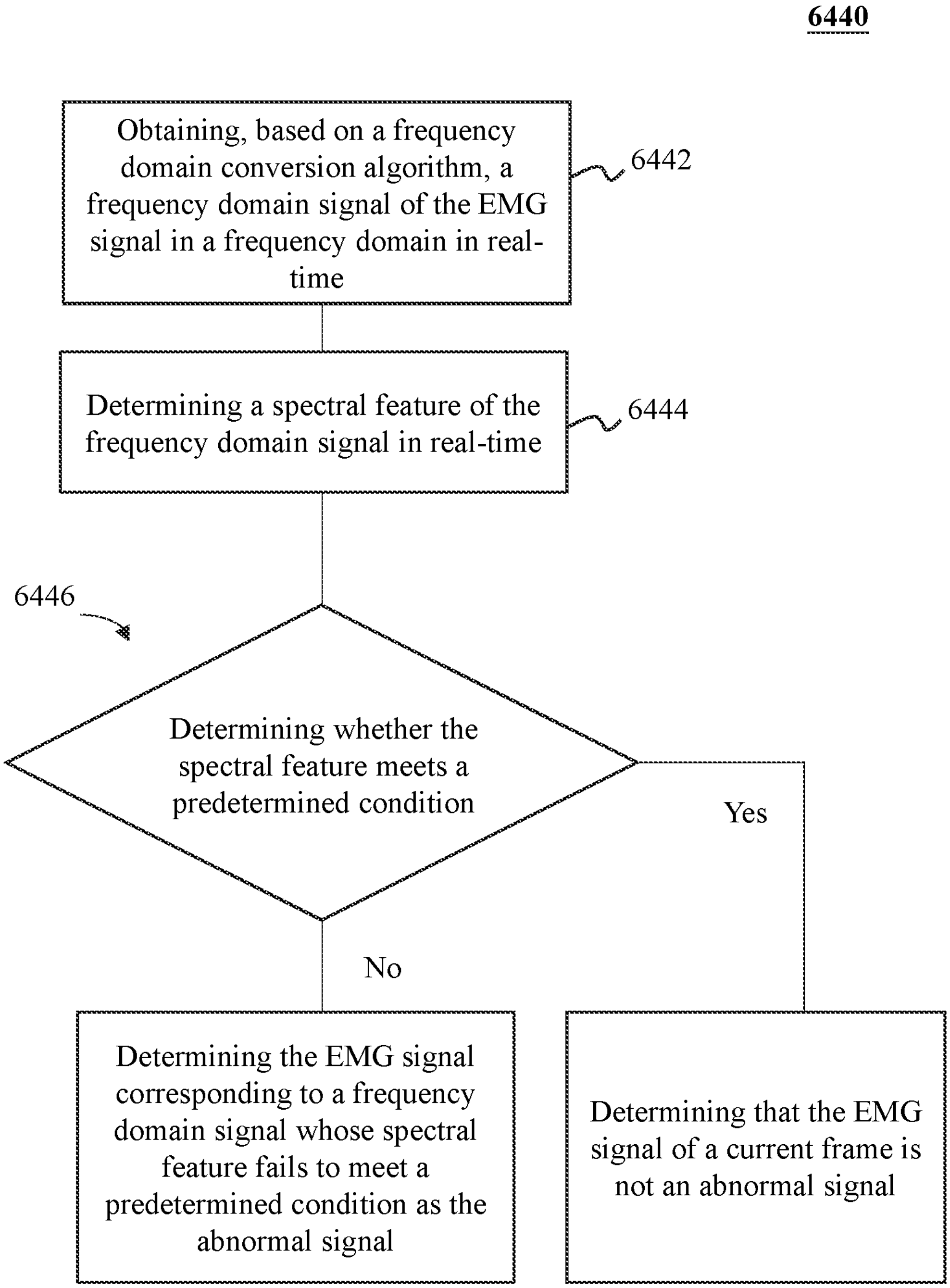
FIG. 16 is a flowchart illustrating an exemplary process for processing an EMG signal in a frequency domain according to some embodiments of the present disclosure.

FIG. 16 is a flowchart illustrating an exemplary process for processing an EMG signal in a frequency domain according to some embodiments of the present disclosure. The operation 6440 is shown in FIG. 16. As shown in FIG. 16, the operation 6440 may include the following operations.

In 6442, a frequency domain signal of the EMG signal in a frequency domain may be obtained in real-time based on a frequency domain conversion algorithm.

The processing module 220 may perform the frequency domain conversion on the EMG signal in a time domain in real-time to obtain the frequency domain signal of the EMG signal in the frequency domain. The frequency domain conversion algorithm may be a Fourier transformation, a wavelet transformation, a Laplas transformation, a Z transformation, or the like. When the processing module 220 executes operation 6442, the frequency domain conversion may be performed by taking each frame of the EMG signal as a basic conversion unit. The processing module 220 may perform the frequency domain conversion on the EMG signal frame by frame.

In 6444, a spectral feature of the frequency domain signal may be determined in real-time.

In some embodiments, the spectral feature may include a spectral shape, a power spectral density, a mean power frequency, a median frequency, a wavelet scale, or any combination thereof. In some embodiments, a frequency distribution of a normal EMG signal may be mainly concentrated in a frequency range of 20-400 Hz. An energy distribution area of a normal EMG signal may be mainly in a frequency range of 50-200 Hz. A statistical mean of a normal EMG signal may be generally a Gaussian-like shape of a single peak. However, a spectral distribution shape of an abrupt signal, such as a glitch signal, may be generally asymmetric, which may be significantly different from the Gaussian-like shape of the normal EMG signal. The frequency of a noise signal caused by a motion artifact may be generally below 20 Hz. However, a frequency of a power frequency signal (that is, a saturation signal) that is collected during detachment of a portion of electrodes of an EMG sensor may be generally distributed at 50 Hz, and a frequency spectrum of the saturation signal may be flatter than that of the normal EMG signal. The spectral feature of the normal EMG signal may be obviously different from that of the abnormal signal. The motion data processing method 6000 may include identifying the abnormal signal from the normal EMG signals based on the spectral feature of the frequency domain signal of the EMG signal. When the processing module 220 executes operation 6444, the spectral feature of the frequency domain signal of the EMG signal of each frame may be determined frame by frame.

In 6446, the EMG signal corresponding to a frequency domain signal whose spectral feature fails to meet a predetermined condition may be determined as the abnormal signal.

When the processing module 220 executes the operation 6446, the spectral feature of the frequency domain signal of each frame of the EMG signal may be determined frame by frame based on the predetermined condition. In some embodiments, the processing module 220 may determine whether the spectral feature of the frequency domain signal corresponding to the EMG signal of a current frame meets the predetermined condition. The spectral feature of the normal EMG signal should meet the predetermined condition. The spectral feature of the abnormal signal may not meet the predetermined condition. The predetermined condition may be a condition obtained based on a statistical feature of a spectral feature of a normal EMG signal. The predetermined condition may be stored in a storage or a disk of the wearable device 130, or may also be stored in the processing device 110, or adjusted based on an actual situation. In some embodiments, the processing module 220 may identify the abnormal signal from the normal EMG signal based on a determination result that whether the spectral feature of the frequency domain signal meets the predetermined condition in the operation 6446, and perform signal correction processing on the abnormal signal. In some embodiments, if the processing module 220 determines that the spectral feature of the frequency domain signal corresponding to the EMG signal of the current frame does not meet the predetermined condition, the EMG signal of the current frame that does not meet the predetermined condition may be determined as the abnormal signal, and the abnormal signal may be processed through the operation 6600 to correct the abnormal signal. In some embodiments, the processing the abnormal signal may include performing signal correction processing on the abnormal signal based on the EMG signal within a specific time range previous or subsequent to the abnormal signal. More detailed description of the operation 6600 may be described in detail in the following description.

In other embodiments, if the processing module 220 determines that the spectral feature of the frequency domain signal corresponding to the EMG signal of the current frame meets the predetermined condition, the EMG signal of the current frame may be not the abnormal signal, the EMG signal may be retained, and the processing module 220 may retain the EMG signal of the current frame.

As shown in FIG. 6, the method 6000 may also include the following operations.

In 6600, the abnormal signal may be corrected.

In some embodiments, the method 6000 may also include performing signal correction processing on the abnormal signal in real-time. Signal correction processing may refer to correction of an abnormal signal (e.g., an abrupt signal, a missing signal, a saturation signal, an oscillation signal, etc.) in the EMG signal. As mentioned, in 6400, the processing module 220 may performed the identification of the abnormal signal in real-time. In 6600, the correction of the abnormal signal by the processing module 220 may also be performed in real-time. That is, the processing module 220 may identify the abnormal signal in real-time and correct the abnormal signal in real-time.

Figure 17:
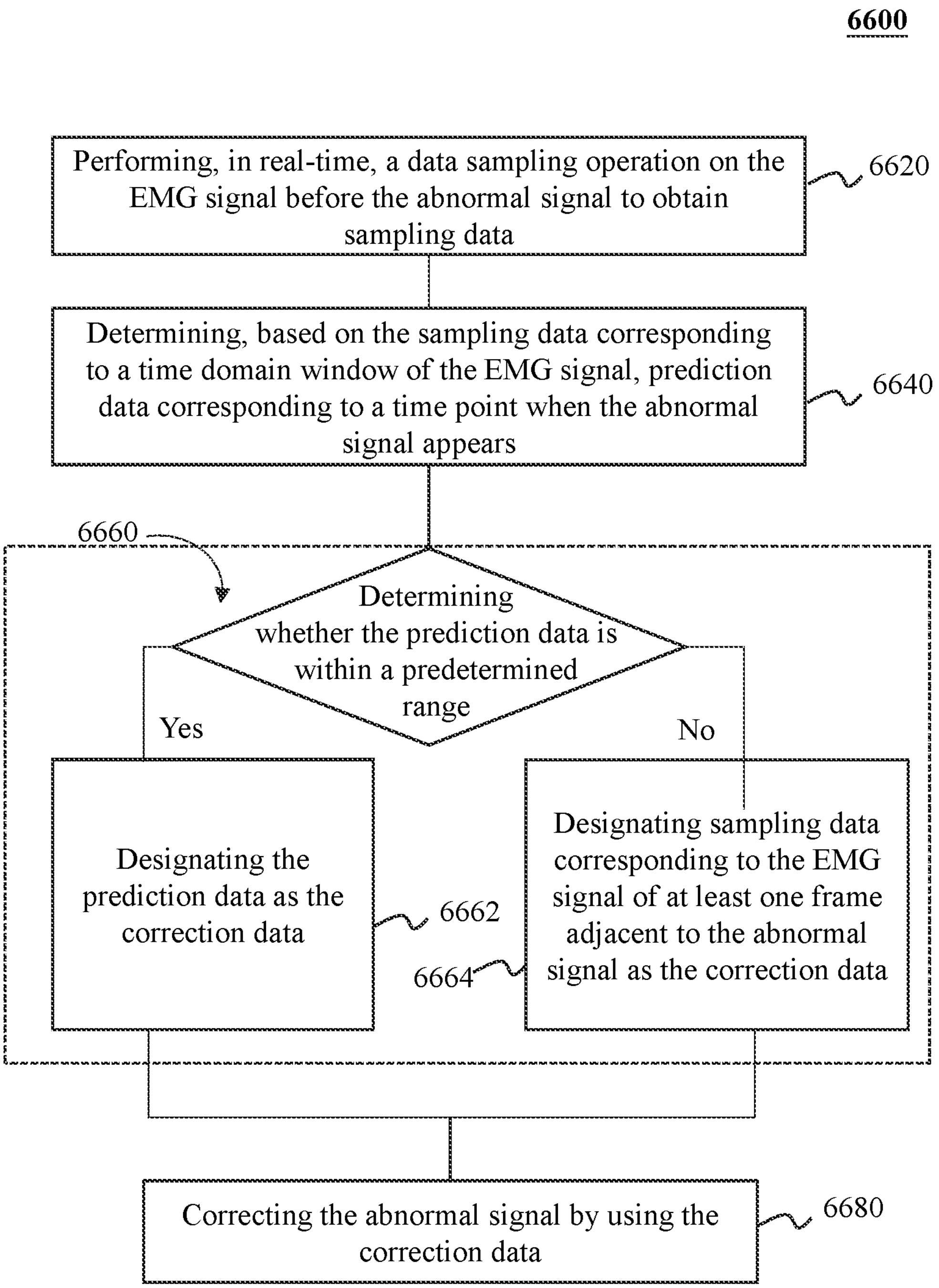
FIG. 17 is a flowchart illustrating an exemplary process for correcting an abnormal signal according to some embodiments of the present disclosure.

FIG. 17 is a flowchart illustrating an exemplary process for correcting an abnormal signal according to some embodiments of the present disclosure. The operation 6600 is shown in FIG. 17. As shown in FIG. 17, the operation 6600 may include the following operations.

In 6620, a data sampling operation on the EMG signal before the abnormal signal may be performed in real-time to obtain sampling data.

As mentioned, the processing module 220 may identify the abnormal signal in real-time and correct the abnormal signal in real-time. That is, when the processing module 220 identifies a new abnormal signal, correction processing may be completed on the abnormal signal before another new abnormal signal. In other words, the EMG signal before a current abnormal signal may be constituted by a normal EMG signal and an abnormal signal that has been corrected, that is, there is no abnormal signal in the EMG signal before the current abnormal signal. In 6620, the processing module 220 may complete the data sampling of the EMG signal before the current abnormal signal in real-time, so as to obtain the sampling data corresponding to the EMG signal before the current abnormal signal.

The data sampling may obtain several discrete data (that is, sampling data) based on the EMG signal through sampling, etc. The sampling data may be discrete data obtained after the data sampling. Specifically, the method of the data sampling include obtaining the discrete data based on a specific time period. The specific time period may have any time length. For example, the specific time period may have a length of one frame, a length of 0.5 frames, or may be shorter. For example, an average of 10, 20, 30, or even more discrete data may be collected in a frame. The discrete data may be statistical data within the specific time period, such as an average an intermediate value of the data within the specific time period, or the like.

In 6640, prediction data corresponding to a time point when the abnormal signal appears may be determined based on the sampling data corresponding to a time domain window of the EMG signal.

The processing module 220 may perform data fitting based on the sampling data to obtain a fitting curve. In some embodiments, the processing module 220 may perform the data fitting on the sampling data based on a fitting function to obtain the fitting curve. In some embodiments, the processing module 220 may also perform the data fitting on the sampling data based on a neural network technique to obtain the fitting curve.

In some embodiments, the operation 6640 may determine, based on the sampling data corresponding to the time domain window, the fitting function; and determine, based on the fitting function, the prediction data corresponding to the time point when the abnormal signal appears. The fitting function may be a curve function in any form. In some embodiments, the fitting function may be a sine function or a cosine function. In some embodiments, the fitting function may be a function of different orders, such as a quadratic function, a cubic function, a quartic function, or the like. An independent variable in the fitting function may be time, and a dependent variable may be an amplitude of the EMG signal. In 6640, the processing module 220 may perform the data fitting based on the sampling data to determine the fitting function and predict the amplitude of the EMG signal corresponding to the time point when the abnormal signal appears based on the fitting function to obtain the prediction data corresponding to the time point when the abnormal signal appears. The prediction data may be the amplitude of the EMG signal corresponding to the time point when the abnormal signal appears.

In some embodiments, the operation 6640 may also include determining, based on the sampling data corresponding to the time domain window and a trained long-short term memory (LSTM) network, the prediction data corresponding to the time point when the abnormal signal appears. The LSTM network may be a recurrent neural network capable of learning a long-term dependency and making a prediction. In some embodiments, the processing module 220 may also determine the prediction data corresponding to the time point when the abnormal signal appears based on other recurrent neural networks, such as a gated recurrent unit (GRU) network, and a recurrent neural network (RNN).

In 6660, correction data corresponding to the time point when the abnormal signal appears may be determined based on the prediction data.

In step 6660, after the prediction data is obtained, the processing module 220 may need to determine whether the prediction data meets a usage requirement, that is, to determine whether the prediction data is a reasonable EMG signal. As mentioned, a normal EMG signal may be generally a relative stable signal. The processing module 220 may determine whether the prediction data is a reasonable EMG signal based on other EMG signals around the prediction data. In some embodiments, the operation 6660 may include the following operations.

In 6662, in response to determining that the prediction data is within a predetermined range, the prediction data may be designated as the correction data, or In 6664, in response to determining that the prediction data is not within a predetermined range, sampling data corresponding to the EMG signal of at least one frame adjacent to the abnormal signal may be designated as the correction data.

The predetermined range may include a data range formed by a maximum value and a minimum value of the EMG signal in the time domain window. Specifically, the processing module 220 may obtain the maximum value and the minimum value of the EMG signal in the time domain window before the abnormal signal, and determine whether the prediction data is between the maximum value and the minimum value. As mentioned, the motion data processing method 6000 may identify the abnormal signal in real-time and correct the abnormal signal in real-time. Therefore, the EMG signal before the abnormal signal may be a set of the normal EMG signal and the corrected abnormal signal. That is, there may be no abnormal signal in the EMG signal before the abnormal signal. Therefore, the EMG signal before the abnormal signal may be the normal and reasonable EMG signal. The processing module 220 may determine whether the prediction data is reasonable by determining whether the prediction data is within the data range formed by the maximum value and the minimum value of the EMG signal in the time domain window before the EMG signal. In some embodiments, when the processing module 220 determines that the prediction data is within the data range formed by the maximum value and the minimum value of the EMG signal in the time domain window before the abnormal signal, the prediction data may be determined as the normal and reasonable EMG signal. At this time, the processing module 220 may correct the abnormal signal by using the prediction data as the correction data. In some embodiments, when the processing module 220 determines that the prediction data is not within the data range formed by the maximum value and the minimum value of the EMG signal in the time domain window before the abnormal signal, the prediction data may be determined as the abnormal or unreasonable EMG signal. At this time, the processing module 220 may not correct the abnormal signal by using the prediction data as the correction data. At this time, the processing module 220 may designate sampling data corresponding to the EMG signal adjacent to the abnormal signal within the at least one frame as the correction data. The sampling data corresponding to the EMG signal adjacent to the abnormal signal within the at least one frame may be a statistical value of a plurality of sampling data, such as an average value, an intermediate value, or the like.

In 6680, the abnormal signal may be corrected by using the correction data.

After the correction data is determined, the processing module 220 may use the correction data to correct the abnormal signal. Specifically, the processing module 220 may use the correction data instead of the abnormal signal.

Figure 18:
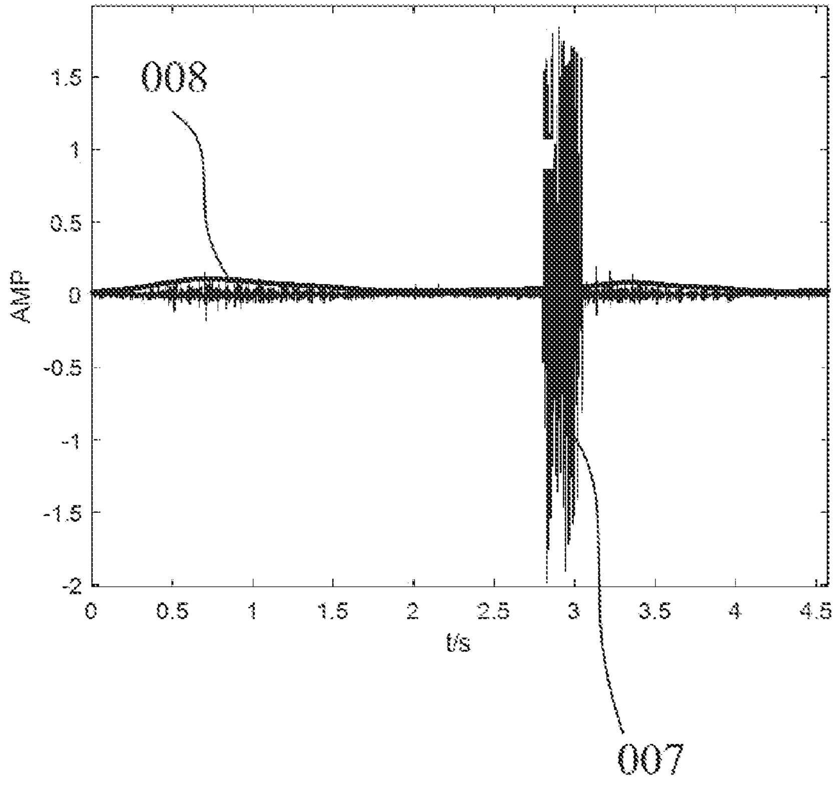
FIG. 18 is a schematic diagram illustrating an exemplary EMG signal and a corrected smooth curve according to some embodiments of the present disclosure.

FIG. 18 is a schematic diagram illustrating an exemplary EMG signal and a corrected smooth curve according to some embodiments of the present disclosure. As shown in FIG. 18, 007 is an EMG signal, and 008 is a smooth curve. The motion data processing method 6000 and the motion monitoring system 100 provided in the present disclosure may process the EMG signal in a frequency domain or in a time domain to identify an abnormal signal in the EMG signal, such as an abrupt signal, a missing signal, a saturation signal, an oscillation signal caused by a high-pass filter, or the like. The motion data processing method 6000 and the motion monitoring system 100 may also perform data sampling on the EMG signal through a data sampling algorithm, and predict data at a time point when the abnormal signal appears based on the sampling data, so as to obtain prediction data and use the prediction data to replace the abnormal signal, so as to correct the abnormal signal. The motion data processing method 6000 and the motion monitoring system 100 may not only accurately identify the abnormal signal, but also correct the abnormal signal, so that the corrected data may be more consistent with the actual motion of the user, thereby improving the user experience.

In some embodiments, the motion data processing method 6000 and the motion monitoring system 100 may also remind the user that the device is abnormally worn in time when the abnormal signal is identified, thereby making the data collection more accurate. For example, when the motion data processing method 6000 identifies the abnormal signal (e.g., a missing signal and a saturation signal), the processing module 220 may send feedback information to the control module 230. The feedback information may feed back that the wearable device 130 may be not properly worn or pulled during the motion of the user. The feedback information may also include prompting the user to adjust the position of the wearable device 130, or the like. The control module 230 may control the input/output module 260 based on the feedback information, and then control the mobile terminal device 140 to send the feedback result of the motion to the user. In some embodiments, the control module 230 may also control one or more sensors or other modules in the acquisition module 210 to provide feedback to the human body. For example, when there is an abnormal signal in the EMG signal corresponding to a certain muscle during the motion of the user, the control module 230 may control the electrode module at the muscle position to electrically stimulate the user to prompt the user to adjust the wearable device 130 in time.

In some embodiments, the performing signal correction processing on the abnormal signal in the EMG signal in the time domain may also include removing a singular point in the EMG signal, for example, deleting the singular point and a signal within a time period near the singular point. Alternatively, the performing signal correction processing on the EMG signal in the time domain may include correcting the singular point of the EMG signal based on feature information of the EMG signal within a specific time range, for example, adjusting the amplitude of the singular point based on a signal around the singular point. In some embodiments, the feature information of the EMG signal may include amplitude information or statistical information of the amplitude information, or any combination thereof. The statistical information (also referred to as an amplitude entropy) of the amplitude information may refer to a distribution of the amplitude information of the EMG signal in the time domain. In some embodiments, after the position of the singular point (e.g., a corresponding time point) in the EMG signal is determined by a signal processing algorithm (e.g., a Fourier transformation, a wavelet transformation, and a fractal dimension), the singular point may be corrected based on the EMG signal within a specific time range previous or subsequent to the position of the singular point. For example, when the singular point is an abrupt trough, the EMG signal at the abrupt trough may be supplemented based on the feature information (e.g., amplitude information, statistical information of the amplitude information) of the EMG signal within the specific time range (e.g., 5 milliseconds −60 milliseconds) previous or subsequent to the abrupt trough.

In some embodiments, the signal correction processing may be performed on the abnormal signal in the EMG signal by using other manners, for example, a high-pass manner, a low-pass manner, a band-pass manner, a wavelet transform reconstruction manner, or the like. In some embodiments, for an application scenarios that is not sensitive to a low-frequency signal, a 100 Hz high-pass filter may be configured to remove a glitch signal. In some embodiments, in addition to performing the signal correction processing on the EMG signal, other signal processing manners may also be performed on the EMG signal, such as a filtering, a signal amplification, a phase adjustment, or the like. In some embodiments, a user's EMG signal collected by the EMG sensor may be converted into a digital EMG signal through an analog-to-digital converter (ADC), and the converted signal EMG signal may be filtered. The filtering process may include filtering out a power frequency signal and a harmonic signal thereof. In some embodiments, the processing of the EMG signal may also include removing a motion artifact of the user. The motion artifact may refer to signal noise generated by a movement of a muscle relative to an EMG module during the motion of the user in the process of obtaining the EMG signal.

It should be noted that the above description regarding the process 6000 is merely provided for the purposes of illustration, and not intended to limit the scope of the present disclosure. For those skilled in the art, various modifications and changes may be made to the process 6000 under the teachings of the present disclosure. For example, the above process 6000 may be only an example in which the abrupt signal is a glitch signal when the abrupt signal is identified and corrected. When the abrupt signal is a trough signal, the above operations and solutions may be adjusted or other methods may be configured to perform signal correction processing. However, those modifications and changes do not depart from the scope of the present disclosure.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. In addition, some features, structures, or features in the present disclosure of one or more embodiments may be appropriately combined.

What is claimed is:

1. A motion data monitoring method, implemented by a wearable device including an EMG sensor, at least one processor and at least one storage medium, comprising:

obtaining, by the EMG sensor, in real-time, an electromyography (EMG) signal corresponding to a measurement position during a motion of a user;

determining, by the at least one processor, in real-time, based on the EMG signal, an abnormal signal in the EMG signal;

automatically controlling, by the at least one processor, an electrode module to electrically stimulate the user to prompt the user to adjust the wearable device in time;

determining, by the at least one processor, in real-time, a corrected EMG signal based on the abnormal signal; and displaying, by the at least one processor, via a user interface, in-real-time, the corrected EMG signal, wherein the EMG signal includes a signal obtained based on a high-pass filtering algorithm, the abnormal signal includes an oscillation signal caused by the high-pass filter algorithm, and the determining, by the at least one processor, based on the EMG signal, an abnormal signal in the EMG signal includes:

determining, by the at least one processor, based on a filter parameter of the high-pass filtering algorithm, the oscillation signal.

2. The motion data monitoring method of claim 1, wherein the determining, by the at least one processor, in real-time, based on the EMG signal, an abnormal signal in the EMG signal includes:

processing, by the at least one processor, the EMG signal in a time domain to determine the abnormal signal.

3. The motion data monitoring method of claim 2, wherein the processing, by the at least one processor, in real-time, the EMG signal in a time domain to determine the abnormal signal includes:

selecting, by the at least one processor, based on a time domain window of the EMG signal, at least one time window from the time domain window of the EMG signal, wherein each of the at least one time window covers a different time range; and determining, by the at least one processor, based on feature information corresponding to the EMG signal in the at least one time window, the abnormal signal.

4. The motion data monitoring method of claim 3, wherein the feature information includes at least one of amplitude information or statistical information of the amplitude information, the statistical information of the amplitude information including at least one of an entropy, a variance, a standard deviation, a standard deviation of the standard deviation, or a zero-crossing rate of the amplitude information.

5. The motion data monitoring method of claim 3, wherein the abnormal signal includes an abrupt signal, the at least one time window includes a plurality of time windows, and the determining, by the at least one processor, based on feature information corresponding to the EMG signal in the at least one time window, the abnormal signal includes:

determining, by the at least one processor, feature information corresponding to the EMG signal in the plurality of time windows; and determining, by the at least one processor, that a ratio of feature information corresponding to a time window subsequent to a time range to feature information corresponding to a time window previous to the time range exceeds a predetermined first threshold, and designating the EMG signal in the time window subsequent to the time range as the abrupt signal.

6. The motion data monitoring method of claim 3, wherein the abnormal signal includes a missing signal, and the determining, by the at least one processor, based on feature information corresponding to EMG signal in the at least one time window, the abnormal signal includes:

determining, by the at least one processor, at least one piece of feature information corresponding to the EMG signal in the at least one time window; and designating, by the at least one processor, the EMG signal in a time window corresponding to feature information that is in the at least one piece of feature information and lower than prestored feature information of a second threshold as the missing signal.

7. The motion data monitoring method of claim 3, wherein the abnormal signal includes a saturation signal, and the determining, by the at least one processor, based on feature information corresponding to EMG signal in the at least one time window, the abnormal signal includes:

determining, by the at least one processor, at least one piece of feature information corresponding to the EMG signal in the at least one time window; and designating, by the at least one processor, the EMG signal in a time window corresponding to feature information that is in the at least one piece of feature information and exceeds prestored saturation feature information as the saturation signal.

8. The motion data monitoring method of claim 2, wherein the EMG signal includes a signal obtained based on a direct current (DC) removing algorithm, the DC removing algorithm including at least one of a de-averaging algorithm or the high-pass filtering algorithm.

9. The motion data monitoring method of claim 8, wherein the processing, by the at least one processor, the EMG signal in a time domain to determine the abnormal signal includes:

determining, by the at least one processor, a reference oscillation height and a reference duration of the oscillation signal based on the filter parameter of the high-pass filtering algorithm; and matching, by the at least one processor, the EMG signal with the reference oscillation height and the reference duration in real-time; and designating, by the at least one processor, the EMG signal corresponding to a signal interval within which the EMG signal matches the reference oscillation height and the reference duration as the oscillation signal.

10. The motion data monitoring method of claim 1, wherein the determining, by the at least one processor, in real-time, a corrected EMG signal based on the abnormal signal includes:

performing, by the at least one processor, in real-time, a data sampling operation on the EMG signal before the abnormal signal to obtain sampling data;

determining, by the at least one processor, based on the sampling data corresponding to a time domain window of the EMG signal, prediction data corresponding to a time point when the abnormal signal appears;

determining, by the at least one processor, based on the prediction data, correction data corresponding to the time point when the abnormal signal appears; and correcting, by the at least one processor, the abnormal signal by using the correction data.

11. The motion data monitoring method of claim 10, wherein the determining, by the at least one processor, based on the sampling data corresponding to a time domain window of the EMG signal, prediction data corresponding to a time point when the abnormal signal appears includes:

determining, by the at least one processor, based on the sampling data corresponding to the time domain window, a fitting function;

determining, by the at least one processor, based on the fitting function, the prediction data corresponding to the time point when the abnormal signal appears.

12. The motion data monitoring method of claim 10, wherein the determining, by the at least one processor, based on the prediction data, correction data corresponding to the time point when the abnormal signal appears includes:

in response to determining, by the at least one processor, that the prediction data is within a predetermined range, designating, by the at least one processor, the prediction data as the correction data, wherein the predetermined range includes a data range formed by a maximum value and a minimum value of the EMG signal in the time domain window.

13. The motion data monitoring method of claim 10, wherein the determining, by the at least one processor, based on the sampling data corresponding to a time domain window of the EMG signal, prediction data corresponding to a time point when the abnormal signal appears further includes:

determining, by the at least one processor, based on the sampling data corresponding to the time domain window and a trained long-short term memory (LSTM) network, the prediction data corresponding to the time point when the abnormal signal appears.

14. The motion data monitoring method of claim 10, wherein the determining, by the at least one processor, based on the prediction data, correction data corresponding to the time point when the abnormal signal appears further includes:

in response to determining that the prediction data is out of the predetermined range, designating, by the at least one processor, sampling data corresponding to the EMG signal of at least one frame adjacent to the abnormal signal within at least one frame as the correction data.

15. The motion data monitoring method of claim 1, wherein the determining, based on the EMG signal, in real-time, an abnormal signal in the EMG signal further includes:

processing, by the at least one processor, the EMG signal in a frequency domain to determine the abnormal signal.

16. The motion data monitoring method of claim 15, wherein the processing the EMG signal in a frequency domain to determine the abnormal signal includes:

obtaining, by the at least one processor, based on a frequency domain conversion algorithm, a frequency domain signal of the EMG signal in the frequency domain in real-time;

determining, by the at least one processor a spectral feature of the frequency domain signal in real-time; and determining, by the at least one processor the EMG signal corresponding to the frequency domain signal whose spectral feature fails to meet a predetermined condition as the abnormal signal.

17. The motion data monitoring method of claim 16, wherein the spectral feature includes at least one of a spectral shape, a power spectral density, a mean power frequency, a median frequency, or wavelet scale.

18. A motion monitoring system, comprising:

an EMG sensor;

at least one storage medium storing at least one instruction set for motion data processing; and at least one processor in communication with the at least one storage medium, wherein when the motion monitoring system is operated, the at least one processor reads the at least one instruction set and implements a motion data processing method, the motion data processing method comprising:

obtaining, by the EMG sensor, in real-time, an electromyography (EMG) signal—corresponding to a measurement position during a motion of a user;

determining, by the at least one processor, in real-time, based on the EMG signal, an abnormal signal in the EMG signal;

automatically controlling, by the at least one processor, an electronic module to electrically stimulate the user to prompt the user to adjust the wearable device in time; and determining, by the at least one processor, in real-time, a corrected EMG signal based on the abnormal signal;

displaying, by the at least one processor, via a user interface, in-real-time, the corrected EMG signal, wherein the EMG signal includes a signal obtained based on a high-pass filtering algorithm, the abnormal signal includes an oscillation signal caused by the high-pass filter algorithm, and the determining, by the at least one processor, based on the EMG signal, an abnormal signal in the EMG signal includes:

determining, by the at least one processor, based on a filter parameter of the high-pass filtering algorithm, the oscillation signal.

19. A wearable device for real-time motion monitoring, comprising:

a base configured to be worn on a body of a user;

an EMG sensor integrated on the base and positioned to contact the user's skin for real-time acquisition of an EMG signal when the wearable device is worn;

a processing module embedded in or physically attached to the base, the processing module comprising at least one processor and at least one storage medium;

wherein the at least one storage medium stores instructions that, when executed by the at least one processor, cause the processing module to perform operations including:

receiving a real-time EMG signal from the EMG sensor, wherein the real-timeEMG signal includes a signal obtained based on a high-pass filtering algorithm;

determine an abnormal signal within the EMG signal, wherein the abnormal signal includes an oscillation signal caused by the high-pass filter algorithm, and the determining the abnormal signal within the EMG signal includes determining, based on a filter parameter of the high-pass filtering algorithm, the oscillation signal;

automatically controlling an electrode module to electrically stimulate the user to prompt the user to adjust the wearable device in time;

determining a real-time corrected EMG signal based on the abnormal signal; and displaying the real-time corrected EMG signal on a user interface, wherein the EMG sensor, the processing module, and the instructions are cooperatively configured to, when the wearable device is worn and operated, achieve real-time acquisition, abnormal detection, and correction of the EMG signal during a motion of the user.

20. The wearable device of claim 19, wherein the wearable device is an upper garment.

* * * * *